(12) United States Patent
Walko

(10) Patent No.: US 12,168,162 B2
(45) Date of Patent: Dec. 17, 2024

(54) CONCAVE ANGULATED POSITIONING DEVICE

(71) Applicant: BYCORE INC., Falmouth, MA (US)

(72) Inventor: Thomas John Walko, Falmouth, MA (US)

(73) Assignee: BYCORE INC., Falmouth, MA (US)

( * ) Notice: Subject to any disclaimer, the term of this patent is extended or adjusted under 35 U.S.C. 154(b) by 780 days.

(21) Appl. No.: 16/881,011

(22) Filed: May 22, 2020

(65) Prior Publication Data

US 2021/0077855 A1    Mar. 18, 2021

Related U.S. Application Data

(60) Provisional application No. 62/822,515, filed on Mar. 22, 2019.

(51) Int. Cl.
*A63B 21/00* (2006.01)
*A61D 99/00* (2006.01)
(Continued)

(52) U.S. Cl.
CPC .......... *A63B 21/4039* (2015.10); *A61D 99/00* (2013.01); *A61F 7/00* (2013.01); *A61G 5/122* (2016.11); *A61G 7/10* (2013.01); *A61G 13/009* (2013.01); *A61H 1/0229* (2013.01); *A61H 19/50* (2013.01); *A61H 23/006* (2013.01); *A61M 21/02* (2013.01); *A61N 2/02* (2013.01);
(Continued)

(58) Field of Classification Search
CPC ............ A63B 21/4039; A63B 21/4037; A63B 21/065; A63B 21/078; A63B 22/0076; A63B 22/0605; A63B 2022/0094; A61G 5/122; A61G 7/10; A61G 13/009; A61D 99/00; A61F 7/00; A61H 1/0229; A61H 19/50; A61H 23/006; A61M 21/02; A61M 2021/0022; A61M 2021/0027; A61N 2/02; A61N 7/00; A61N 5/067; A61N 2005/0651; A61N 2005/0659; A61N 2005/0661; A61N 2005/1087; A47C 20/021; A47C 20/027

See application file for complete search history.

(56) References Cited

U.S. PATENT DOCUMENTS 3,628,790 A * 12/1971 Gordon .................... A63B 6/00
                                                         482/25
4,579,111 A *  4/1986 Ledesma ................ A61G 13/12
                                                         128/845

(Continued)

*Primary Examiner* — Steven O Douglas
(74) *Attorney, Agent, or Firm* — Panitch Schwarze Belisario & Nadel LLP

(57) ABSTRACT

An improved positioning device ("the DEVICE") comprises a new and unique concave angulated device for at least one of, but not limited to, stretching, supporting, bracing, rehabilitating, positioning, massaging, kneading, scratching, or exercising a body of a user. The DEVICE's new concave angulated and more user friendly surface addresses the need for a more anatomically responsive body positioning DEVICE for achieving improved results relative to, among other things, the above uses. This DEVICE includes multiple embodiments, which also may comprise various possible configurations, that enable the DEVICE to also function as a fulcrum or lever and/or be capable of uniquely dispersing a load during the interaction between the user and the DEVICE.

29 Claims, 16 Drawing Sheets

(51) Int. Cl.

| | |
|---|---|
| *A61F 7/00* | (2006.01) |
| *A61G 5/12* | (2006.01) |
| *A61G 7/10* | (2006.01) |
| *A61G 13/00* | (2006.01) |
| *A61H 1/02* | (2006.01) |
| *A61H 19/00* | (2006.01) |
| *A61H 23/00* | (2006.01) |
| *A61M 21/02* | (2006.01) |
| *A61N 2/02* | (2006.01) |
| *A61N 5/02* | (2006.01) |
| *A61N 7/00* | (2006.01) |
| *A63B 21/065* | (2006.01) |
| *A63B 21/078* | (2006.01) |
| *A63B 22/00* | (2006.01) |
| *A63B 22/06* | (2006.01) |
| *A47C 20/00* | (2006.01) |
| *A47C 20/02* | (2006.01) |
| *A61M 21/00* | (2006.01) |
| *A61N 5/06* | (2006.01) |
| *A61N 5/067* | (2006.01) |
| *A61N 5/10* | (2006.01) |

(52) U.S. Cl.
CPC ............... *A61N 5/02* (2013.01); *A61N 7/00* (2013.01); *A63B 21/065* (2013.01); *A63B 21/078* (2013.01); *A63B 21/4037* (2015.10); *A63B 22/0076* (2013.01); *A63B 22/0605* (2013.01); *A47C 20/021* (2013.01); *A47C 20/027* (2013.01); *A61M 2021/0022* (2013.01); *A61M 2021/0027* (2013.01); *A61N 2005/0651* (2013.01); *A61N 2005/0659* (2013.01); *A61N 2005/0661* (2013.01); *A61N 5/067* (2021.08); *A61N 2005/1087* (2013.01); *A63B 2022/0094* (2013.01)

(56) References Cited

U.S. PATENT DOCUMENTS

| | | | | |
|---|---|---|---|---|
| 6,154,903 | A * | 12/2000 | Wai-Chung | A47C 20/026 5/640 |
| 6,324,710 | B1 * | 12/2001 | Hernandez | A61G 13/0054 5/639 |
| 10,130,836 | B2 * | 11/2018 | Madion | A63B 21/4039 |
| 2012/0214653 | A1 * | 8/2012 | Tsou | A63B 21/00047 482/142 |
| 2012/0304388 | A1 * | 12/2012 | Sever | A47G 9/10 5/636 |

\* cited by examiner

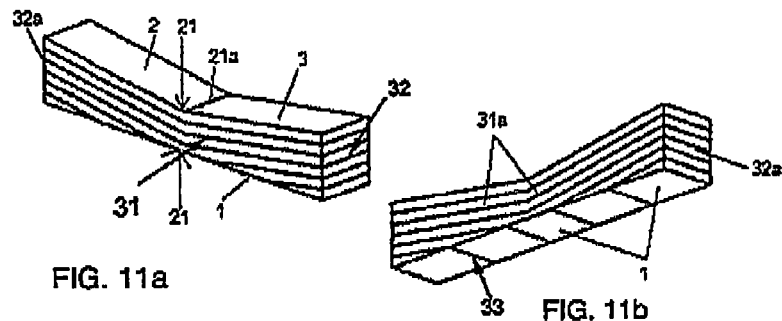
FIG. 11a  FIG. 11b
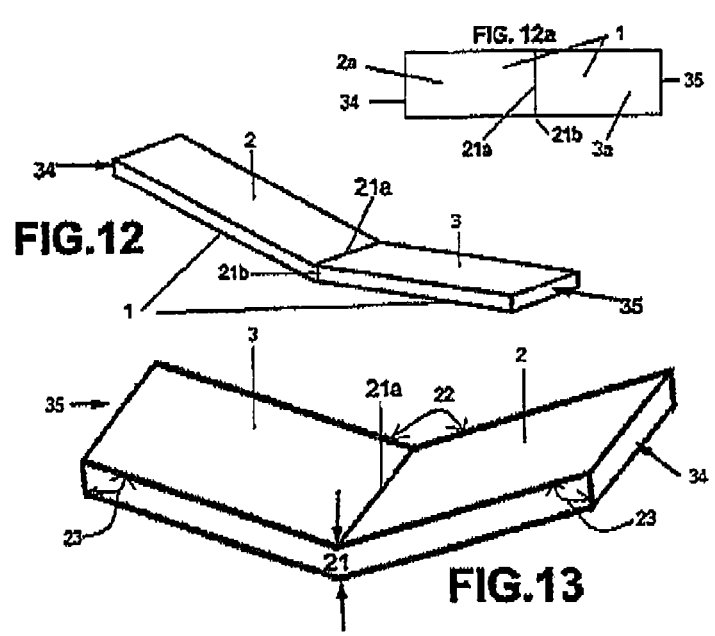
FIG. 12
FIG. 13

CONCAVE ANGULATED POSITIONING DEVICE

CROSS-REFERENCE TO RELATED APPLICATIONS

This application claims the benefit of U.S. Provisional Patent Application No. 62/822,515, filed Mar. 22, 2019, which is incorporated by reference herein in its entirety.

FEDERALLY SPONSORED RESEARCH

None.

SEQUENCE LISTING

None.

BACKGROUND

The present disclosure consists of a new user-friendly concave angulated device ("DEVICE") comprising of an overall concave angulated shape which may also function as a fulcrum or lever and/or be capable of uniquely dispersing a load during the interaction between user and the DEVICE. The DEVICE also includes multiple embodiments of design, manufacturing options and/or of combinations of varieties of materials, dimensions, structural orientations, internal mechanisms, performance options, performance capabilities, and/or densities to accommodate the various uses and/or body parts that interact with the DEVICE during use.

At least one concave angulated surface of the DEVICE further comprises the following embodiment: at least one concave angulated surface comprising, at least one, but not limited to, two connected surfaces within the overall concave angulated surface that, among other things, are at least substantially flat, and thus form, but are not limited to, at least one substantially dihedral edge (i.e. a line of intersection between two surfaces that form a dihedral angle) or when there are more than two connected surfaces within the overall concave angulated surface that, among other things, are at least substantially flat, and thus form several substantially dihedral edges, and also aids in creating a polyhedral presentation. The DEVICE incorporates one or more surfaces that the user's body comes into contact with during use, thus comprising a user contact composite surface. Furthermore, the novel user-friendly concave angulated user contact composite surface, which includes multiple embodiments, refers to concave surfaces, which are similar to dihedral angled surfaces, connecting to form edges, which for descriptive purposes the depression portion of these surfaces may also be referred to in this application as a concave angulated dihedral valley and/or a valley when there is one connection between concave surfaces, and concave angulated dihedral valleys and/or valleys when there are more than two concave angulated surfaces forming more than one connection. These multiple concave angulated surface connections or valleys may also form contrasting peaks or ridges, seen in polyhedral orientations, including, but not limited to, where the concave surfaces connect to one of the other side surfaces within the various embodiments.

Manufacturing a similar device is conceivable to be designed to mimic at least one aspect of the DEVICE's at least one concave angulated surface embodiment, function, and/or use by creating in effect a similarly functioning device from a non concave angulated surface and/or from an overall horizontal, cylindrical, rounded, and/or convex surface orientation and in effect allow the inner portion to produce the net effect of the DEVICE and/or the DEVICE's concave angulated surface's aspects relative to at least one of the many statements, embodiments, implications, and/or claims presented directly or indirectly in this application. This application further states that the net effect of the DEVICE-user interaction producing the overall effect and/or function of the DEVICE and/or DEVICE's concave angulated surface is also incorporated within this application. Furthermore, the net effect of the interaction of the device with the user also comprises, among other things, but not limited to, the production of at least one of an effect, a result, a formation, a purpose, a quality, an action, a reaction, an interaction, a resemblance, or a design that also functions as, but not limited to, at least one of the many uses of the DEVICE or at least one possible method of use of the DEVICE.

The DEVICE is also unique and new because of, but not limited to, its at least one concave angulated surface which is a primary surface of interaction with a user and can be, among other things, positioned against, under, or behind various parts of the user's body, and/or be attached to an apparatus which may greatly benefit the user including areas of the anatomy that are better accessed by interaction with the DEVICE's angulated surface(s) during use to assist and/or improve the function of those areas. The base surface of the DEVICE may be, among other things, positioned against at least one of a solid surface, a weighted object, held, and/or positioned, such that the DEVICE's concave angulated surface can interact with the user's body with sufficient interaction to encourage use of the DEVICE. The DEVICE's side surfaces, including which could be considered the front, rear, right, base, and left side surfaces, are also unique with their variable dimensions, and/or angles of the various surface connections, dihedral surfaces, and/or polyhedral presentations to allow a use of at least one of, but not limited to, the DEVICE's multiple embodiments and/or uses.

The positioning DEVICE, specifically a concave angulated positioning device, incorporates a design that allows users to better position such a device against various parts of the user's body to assist and improve the function of those areas. There is a need for such a device as its improved utilities can greatly benefit many healthcare providers, physical therapists, and body and exercise trainers recognize the benefits of core strength which includes balance and movement abilities, especially of the spine-pelvic-hip regions. Core strength in general is a descriptive term used by the healthcare industry which refers to those muscles primarily in the spine, torso, abdominal, waist, thoracolumbopelvic spine, and/or pelvic-hip region.

The core muscles may include, but not limited to, the psoas major, psoas minor, iliopsoas, pelvic floor muscles, obturator internus, transversus abdominis, multifidus, internal obliques, external obliques, rectus abdominis, erector spinae (sacrospinalis) especially the longissimus thoracis, and the diaphragm; also, the lumbar muscles, posterior chain, anterior chain, quadratus lumborum, deep rotators, as well as cervical muscles, scalenes, rectus capitus anterior and lateralis, longus coli, may also be considered members of the core group, as well as the latissimus dorsi, gluteus maximus, hip muscles, and trapezius.

Core muscles generally function for a multitude of body movement patterns especially those of balancing the body while locomoting, hunting, fighting, changing positions, or being still. They can do so because core musculature are almost entirely anatomically right and left sided, bilateral, as well as at least partially anterior and posterior relative to the spine, pelvis, and related extremities like the hips. The lumbar spine naturally adopts a lordotic curve after weight bearing begins during the progression of infancy. The angle of the pelvic innominate bones develop at wing-like angles folded forward from the sacrum toward the front of the hips basically forming a dihedral angle when one looks downward at the pelvis with a horizontal reference line passing across the front of the pelvis, similar to the path of a belt across the front of one's waist.

The DEVICE also includes at least one embodiment where the described at least one concave angulated surface also essentially produces a dihedral angle or edges which allows the DEVICE to perform as a more anatomically friendly positioning device, see FIGS. 28 and 29 relative to the pelvic anatomy as well as the overall anatomy of the body, torso, spine, and extremities. This concept of anatomically friendly design is further discussed in the section regarding backpack apparatus incorporation.

Many motions including exercises, stretches, as well as movements of the spine, core, extremities, and hips encourage and/or facilitate balance movements, development of improved posture, and/or emphasize improved movement abilities are considered valuable movements. In addition, many healthcare and fitness facilities, schools, athletic teams, and homes are equipped with devices, which do not have this unique design, which rely on strengthening, stretching, balancing, and/or treating the user's spine, extremities, hips, shoulders, knees, elbows, ankles, wrists, hand, fingers, feet, toes, muscles, joints, ligaments, tendons, neuromusculoskeletal system, circulatory system, lymphatic system, and/or core for improved function. This application proposes that the DEVICE and its embodiments will significantly aid users in achieving their goals.

As particular activities of daily living and ergonomics force a person to balance and assume proper posture, the numerous muscles, and skeletal system used to maintain balance, core, and posture are strengthened by fitness and rehabilitation movements and exercises. These stronger muscles may improve a person's balance FIG. 23, movement, and posture. Thus, exercises that encourage persons to strengthen theses balancing and gross movement muscles, which couples core strength FIG. 27 to spine-pelvic-hip flexibility FIG. 28, act as possibly the most important link between the upper and lower body and produce improved posture, movement, and flexibility, ameliorate pain pathways, and are considered valuable exercises.

Furthermore, the DEVICE is unique with regards to how it helps improve, redefine, and/or modify present convention for similar devices related to body positioning, exercise, supporting, bracing, rehabilitation, massaging, and/or stretching, which primarily involve the limitations of using a conventional convex, concave rounded, rounded, and/or cylindrical positioning and/or "foam roller" style device to be used against and/or on an area of the body and/or have the device roll against the body of a user. The user's body is essentially tubular or cylindrical in the extremities and larger and more round in the torso, which interaction with a foam roller, cylindrical, round, or sphere positioning device would most likely result in a more tangential physical interaction rather than a more cradling and anatomically friendly interaction as is possible and more probable with the DEVICE. The new improvement is based on the DEVICE'S different concave angulated user contact composite surface and other embodiment configurations. The use relative to these conventionally shaped device interactions including their more limited resultant effect of simply compressing tight, whether contractile or non contractile, and/or painful body tissues at the tangential point of the rounded and/or convex device, similar to that of the simple action of a rolling pin, and/or a ball, moving over dough as when for example rolling out pizza dough. Also, bodily tissue is different from dough, which dough can be easily stretched into a flattened and longer orientation which mostly stays close to the distance it is rolled out to when the rolling pin is pushed downward and rolled over the dough, thus a kneading action is accomplished by the stretching. Whereas, bodily tissues can easily and almost immediately return to their original orientation once the rolling pin moves off the tangential point. The DEVICE proposes to maintain a substantially longer period of physical interaction with the bodily tissues than the roller or sphere devices because of the DEVICE's surface uniqueness, resulting in a prolonged stretching, rubbing, kneading, scratching, and/or massaging of the tissues, primarily the muscular tissues as well as the fat tissues.

The rolling pin action is at least effective for momentarily stimulating at least the pain signalling nociceptors which signal pain messages to the brain of the user indicating they are rolling on a painful tissue, as well as a more limited massage effect than the DEVICE because the roller moves quickly off the tissue while the DEVICE can easily maintain in effect continued interaction with the movement of the tissues. The DEVICE is designed to, among other things, maintain contact with the user while the DEVICE is being moved, in motion, and/or when the user is moving against the DEVICE, which for instance occurs when the user performs a rolling type of movement against the DEVICE, as with a foam roller for instance. Also, this in effect maintaining physical contact with the DEVICE-user interaction occurs after the user positions the DEVICE against their body or when another apparatus or person positions the DEVICE against the body of another user, which would be typical of, but not limited to, a clinical situation as the healthcare provider could essentially massage or otherwise provide therapy to the user with one of the many embodiments of the DEVICE.

With the rolling pin action of conventional foam rollers or balls and the like, the user often rolls back and forth on this tight, whether contractile or non contractile, and/or painful tissue, and there is a resultant possible continued cycle of restimulation and de-stimulation of the pain message producing nociceptors when the foam roller or ball is rolled away from that painful tissue and then back onto it. This rolling and moving off and then back onto the painful tangential point, among other things, decreases the possibility of timely or quickened pain relief.

An inherent disadvantage of the rolling pin repeated fluctuations of rolling compression is likely reduction in the accommodation of the stimulation of nociceptive pain messages from that tangential tissue. Furthermore, this decreases the possibility of properly stimulating other pain blunting non-pain-producing endorphin stimulating mechanoreceptors, directly and/or indirectly, relative to the painful and/or tight, whether contractile or non contractile, initial tangential tissues. This is due to decreasing the possible endorphin stimulating mechanoreceptors activity resulting in less pain from, among other things, endorphin release, the activation of the descending inhibitory pathways, and/or neurologic competition among the pain and non-pain-producing afferents, to have a beneficial effect on the tight, whether contractile or non contractile, and/or painful tissue initially interacted with at the tangential point of the roller, which helps ease pain, tightness and/or spasmed tissues in the area desired to be assisted.

In comparison, a use of the DEVICE with, for instance, an oscillating, massaging, and/or kneading motion instead of a rolling on and off of the tissues motion as referred to in this application as with a roller, rounded, convex, cylindrical, and/or ball example significantly helps maintain a continued interaction with the entire volume of the tissues of the user against the DEVICE and/or the DEVICE against the user.

The DEVICE's, among other things, unique capacity to help maintain a continued interaction with the user's tissues FIG. 29 when utilizing, but not limited to, an oscillating massaging motion, essentially a dragging and/or stretching of the tissues rather than rolling over and mostly compressing the tissues, is proposed to have, but not limited to, a mostly opposite effect compared to the rolling pin or round type of devices referenced above. The DEVICE introduces a more timely balance of nociceptive pain stimulation by compression with the DEVICE's unique and new user interaction resulting in a possible cascade of net increase of relatively more stimulation of the endorphin releasing and other possible pain dampening neurological pathways discussed above, a more timely decreased pain response, hastened tissue repair, and/or improved tissue recovery process.

The DEVICE's actions with the user FIGS. 28 and 29 are also unique when the interaction is at least one of, but not limited to, an oscillating, massaging, kneading, scratching, rubbing, or stretching motion with the user's tissues helping to maintain a possible continued interaction with the tissues while the DEVICE is moved against the user's tissues and/or when the user moves against the DEVICE. These types of interactions can create an oscillating, massaging, kneading, scratching, rubbing, and/or stretching effect on the tissues which stay in interaction with the DEVICE's user contact composite surface as the continued back and forth movement with the tissues over the distance of the oscillation rather than rolling off one tangential point to another tangential point. For instance, if the user rubs and/or kneads the DEVICE on their thigh in an oscillating motion to create a self massage over a 1 to 3 inch distance, the pressure and gentle friction of the user contact composite surface of the DEVICE with the user's thigh tissues will considerably help maintain a continued interaction with the tissues and move the tissues as well as the DEVICE the same 1 to 3 inches.

The distance traveled is relative to the interacted tissue's pliability; therefore, if the tissues are minimally pliable then the distance the DEVICE travels may be less, for instance 1 inch, and if the tissues have more pliability and/or high fat content then the tissue may travel several inches before end range of that tissue's pliability is encountered and the oscillating movement direction of travel ends at which point the oscillation is then reversed to return in the opposite direction, again for instance, to travel back 1 to 3 inches before once again reversing the direction of massaging oscillation. As this rubbing, oscillating, and/or massaging like movement continues to move the volume of tissues with the movement of the DEVICE over a distance, a time frame, and/or with a frequency the stimulation of the tissue's, among other things, but not limited to, endorphin releasing and/or other possible pain dampening neurological pathways which may have been discussed above, are encouraged with a possible, at least one of, but not limited to: resultant cascade of a more timely net decreased pain response relative to the compressed pain producing nociceptors and/or other painful aspects of that tissue, hastened tissue repair, decreasing fluid accumulation, improving fluid drainage, improving circulation, improving lactic acid equilibrium, improving lymphatic flow, improve tissue drainage, improving tissue elasticity of the user, improved tissue recovery process, or other benefits which may or may not have been discussed in this application.

One of the DEVICE's many embodiments and/or actions with the user includes, among other things, that when the DEVICE is placed FIG. 29, for instance, against the outer thigh, the iliotibial band (IT Band), and/or the buttocks a different type of compression interaction with the user occurs with the DEVICE. Some of these differences, including the various embodiments described in this application, are of varying options for materials, densities, orientations (see multiple FIGS.), designs, functional capacities, surface variations, angulation variations, variations in dimensions of the various surfaces, combinations of different aspects of the various embodiments, and/or development to include having the unique capacity to better maintain an overall continued physical interaction with the volume of the user's tissues along the DEVICE's positioning against this interaction's surface area whether the user or DEVICE is essentially not moving and/or if the user or DEVICE is essentially moving. The possible continued physical interaction with the movement along the shared DEVICE-user-tissues surface's interaction is a relatively more involved resulting motion than similar interactions of a foam roller, ball, rounded, and/or an overall convex user contact composite surface and tissues interaction.

Furthermore, the DEVICE is proposed to better maintain tissue interaction during DEVICE-user movement of, among other things, an oscillating, a kneading, scratching, a rubbing, and/or a massaging action that also may be at least one of dragging, stretching, or moving the majority of this interaction with the volume of tissue along the interaction with the DEVICE's concave angulated surface(s) FIGS. 17-26. This interaction may also be described, for instance, as an oscillating like movement over a distance and at a frequency which may subsequently better and/or more dramatically stimulate non-pain-producing mechanoreceptors and/or other neurologic tissues related with the interacted tissues, both stimulated directly and/or indirectly, whether the user is actively moving their body against the device and/or if the user and/or another apparatus and/or force is moving and/or oscillating the DEVICE against a volume of tissues.

To understand the difference of how the DEVICE better moves the volume of tissues as compared to the rolling pin analogy it is helpful to visualize a large clump of sea vegetation swaying in the ocean current where the sea vegetation movement represents a lever as well as the user's tissues, including muscle and fat. The sea vegetation swaying or moving with a back and forth oscillating motion of the water both toward and away from the shoreline is analogous to the tissues moving in a swaying or oscillating motion with the movement of the user-DEVICE's more constant and continued interaction. The vegetation is rooted into the floor or bed of the ocean, like a fulcrum, and does not move, yet the ends of the vegetation sway with the ebb and flow of the ocean water. The lever here is also analogous to the upright handle or user tissues of a manually operated railroad track switch and the apparatus it pivots on is the fulcrum or device. The user's tissues, for instance, are secured or rooted to the underlying musculoskeletal bed or skeletal tissues while the layers of tissue and/or muscle tissues that are farther away from their secured boney bed can; thus, move more freely against their interaction with the DEVICE-tissue ocean current-like movement. This swaying movement may be produced by a user to be rhythmic and soothing, as with a rocking a baby to sleep analogy, is what is meant by movement of the volume of the tissues with the, at least but not limited to, oscillating, rubbing, kneading, scratching, and/or massaging action of the DEVICE against the user's tissues. Rather than simply moving a rolling pin or, to be more dramatic, a pavement roller over the clump of sea vegetation to produce a positive effect of that expected by the massaging of this same tissue, the result is more of a rolling pin over tissue producing a painful compression of neurological response and where an expected timely desired result by the rolling pin or rolling a ball over a user being massaged is challenged in comparison by this application. This application proposes that the simple rolling of the tissues, especially muscular tissues more than fat, are more or less simply being compressed and not specifically kneaded, which is mostly required to constitute being massaged because the roller or spheres roll off and back onto the tissue and does not maintain interaction with the tissue to drag, move, and/or knead it properly.

The analogous ebb and flow of the water is modulated by the ocean's current, whether strong or gentle, just as the rubbing or other like motion interactions with the DEVICE-user tissue FIG. 29 is primarily determined by the user as well as their choice of DEVICE embodiment designs and/or the portion of a concave angulated surface to be placed against their tissues. Also, for instance, the desired user tissue pressure against the angular edges taller FIG. 7 and/or deepest portion(s) FIGS. 19-21, 24, and 25 produces a different effect on the user than choosing to place tissue pressure against the most angulated peak of the user contact composite surface FIG. 26 ridge 111 of the DEVICE. A similar choice is made based on the various other embodiments, but not limited to, such as various materials, densities, internal layer orientation, laminated orientations, overall design differences, dimensional ranges, edges angle ranges, connections, apparatus interactions, size, and/or method of use differences.

Additionally, the possible continued connection and/or interaction with the oscillation of tissues, as opposed to the rolling on and off of the painful tissues with the previous foam roller example, provides the opportunity for the competing non-pain-producing mechanoreceptive endorphin releasing stimulating afferent actions to possibly produce, but not limited to, crowding out of nociceptive afferents at and subsequent to their transmission to the dorsal horn of the spinal column and/or enough stimulation of endorphin release to counteract the stimulation of the painful nociceptors by the user's movement in the nervous system. Also, the DEVICE includes embodiments with the potential to be made of soft materials that perform in a firm manner such that if the user chooses to position the DEVICE or themselves against the DEVICE then less pressure is potentially experienced. This described more involved user-DEVICE interaction may result in, but may not be limited to, a much greater response by a net effect of pain reduction and tight, whether contractile or non contractile, muscle inhibition neurological cascade of the tissue's additional stimulation of non-pain-producing mechanoreceptor's endorphin stimulation and/or competition with stimulated compressed painful nociceptive afferents along their possibly shared afferent pathways, including any favored non-pain-producing mechanoreceptive competition locally, at the dorsal horn of the spinal cord, and/or subsequent central neurologic pathways with the tissue's nociceptive transmission of pain, or painful result, and subsequent proposed non-pain-producing mechanoreception stimulation of, among other things, endorphins, opioid release, stimulation of the descending inhibitory pathways, and/or depression or inhibition of pain producing Substance P, which are involved with the described movement of the entire volume of tissues, whether directly or indirectly, by the user's interaction with the DEVICE.

Some of the tissues affected in this proposed way by use of the DEVICE may include, but are not limited to: at least one of passive spinal intervertebral disc (disc) decompression, active spinal intervertebral disc decompression, passive spinal intervertebral disc flexion distraction, active spinal intervertebral disc flexion distraction, passive spinal intervertebral disc extension distraction, active spinal intervertebral disc extension distraction, spinal disc pump action, spinal intervertebral disc imbibition, spinal intervertebral disc repair, spinal intervertebral disc hydration, spinal intervertebral disc inflammation reduction, spinal intervertebral disc debris reduction, spinal joint anatomic effects, spinal joint physiologic effects, spinal traction, extremity joint anatomic effects, extremity joint physiologic effects, joint decompression, joint hydration, joint repair, joint distraction, joint traction, muscle repair, muscle stretching, muscle elongation, muscle strengthening, muscle relaxation, muscle spasm relaxation, tendon repair, tendon stretching, tendon strengthening, ligament repair, ligament strengthening, ligament stretching, cartilage repair, cartilage hydration, disrupting scar tissue, disrupting the formation of scar tissue, elongating scar tissue, elongating neurological tissues, decreasing fluid accumulation, improving fluid drainage, improving circulation, improving lactic acid equilibrium, improving lymphatic flow, improve tissue drainage, improving tissue elasticity of the user, afferent stimulation of impulses from the periphery to the central nervous system, neurological tissue, the release of endorphins, activation of the descending inhibitory pathways, the subsequent depression and/or inhibition of contractile tissues, the subsequent depression and/or inhibition of pain promoting tissues, the subsequent sense of relaxation of the body, the subsequent sense of relaxation of the mind, the subsequent sense of relaxation of the spirit, or the subsequent sense of relaxation of the soul of the user.

Furthermore, exercises with a use of the DEVICE that also allow the user to engage in active hip adduction FIG. 29, with or without oscillating movement, increase concentric and isometric hip adductor muscle activity which possibly results in a responsive neurologic activation for improved posture, movement, flexibility, and/or amelioration of pain pathways. Additionally, in the instance that the method of use includes the user lying on, among other things, their down side with the device against, but not limited to, a thigh, and/or hip and the user actively, among other things, oscillates in a head to toe massaging and/or kneading manner against the tissues while they may or may not actively perform hip adduction movements on the side they are lying on. This motion possibly incorporates primarily, but not limited to, a contraction of the same hip adductor muscles the user is lying on the DEVICE with to possibly further stimulate a synergistic depression and/or inhibition of the down side hip abductors which are being in effect oscillated against during a more continued interaction with the stable DEVICE. The down side referred to above is the portion of the body that is orientated towards the surface that is providing the normal force to the DEVICE and user, for instance, when laying on the outside of the left leg on the floor or against a wall, the outside of the left leg would be considered the down side.

The DEVICE may maintain stability which in the proposed instance above is on the floor and positioned along the side lying user's FIG. 29 lateral hip, thigh, buttock, iliotibial band, knee, and/or leg resulting in an additional neurologic signaling from the tight, whether contractile or non contractile, tissues on, at least but not limited to, this lateral lower extremity to, but not limited to: relax, improve function, repair, recover, rehydrate, undergo some degree of pain relief, and/or feel better. More benefits may be resultant improvement of muscle hydration, rehydration of proper muscle fluids, improved circulation, improved lymphatic flow, as well as assisting normalization of lactic acid levels in the related tissues.

Additionally, exercise methods with the DEVICE may also benefit from the proposed net pain reduction and tight, whether contractile or non contractile, muscle inhibition neurological cascade, and other benefits described in this application, as well as unique strengthening and/or stretching effects, from a proposed use or uses of the DEVICE. The production of a net responsive relaxation and pain competing process resulting in the user experiencing less pain in the desired area of use as described above is furthermore proposed to be a subsequent result of an active use of the DEVICE, for at least but not limited to, exercising against the unique DEVICE. For instance, when the supine user places the DEVICE under the upper lower lumbar spine, pelvis, and/or hips and performs active core or hip exercises the user's rounded shape of their back, torso, rib cage, spine, hips, and/or pelvis is more comfortably cradled by the more anatomically user friendly at least one concave angulated surface of the DEVICE possibly because, but not limited to, the at least one concave angulated user contact composite surface may act as a fulcrum, lever, and/or be capable of uniquely dispersing a load during the interaction between the user's rounded areas of interaction and the DEVICE.

In contrast, when the user chooses a conventional more horizontal foam roller, cylindrical device, rounded surface, and/or spherical device to be placed against the user's more rounded shaped back, torso, rib cage, spine, hips, and/or pelvis those tissues undergo a more compressed, a more tangential, and thus potentially more painful or restrictive producing interaction when, at least but not limited to, the user conducts active and/or passive movements for exercise, stretching, and/or foam rolling like motions relative to using the DEVICE. The DEVICE's design also allows for use from a greater age range of users, including geriatric aged people. This contrasting relationship is proposed because of the DEVICE's unique embodiments of numerous design and manufacturing options allow for the more anatomically friendly cradling of the at least one concave angulated user contact composite surface as well as the proposed interaction(s) as compared to the conventional options described in this document which require a far greater range of motion, especially when lying supine on an exercise ball or a foam roller, than is expected from the typical geriatric person. Also, because the DEVICE is a proposed possible improvement to a concave rounded device, in comparison a possible concave rounded style device would tend to compress in a more curved wrapping and thus laterally encompassing, constricting, and compressing manner which is more likely to create a less positive result of use.

Additionally, the net pain reduction, and/or tight (whether contractile or non contractile) muscle inhibition neurological cascade effect, when exercising and/or stretching while using the DEVICE may also be heightened by and/or hastened by the additional DEVICE-user interaction's stimulating effect on the non-pain-producing mechanoreceptors in that the volume of tissues as well as those tissues interacted with, directly and/or indirectly, by the movement and interaction of the user's tissues and the DEVICE, among other things, may stimulate subsequent non-pain-producing mechanoreceptor stimulation of opioid release and stimulation of the descending inhibitory pathways, as well as possible painful Substance P release depression and/or inhibition, to initiate relaxation of the sore and/or tight (whether contractile or non contractile) tissues interacted with by the user in comparison to the more tangential compressive rolling pin action of traditional roller devices. This proposed beneficial cascade of neurologic occurrences is quite similar to those proposed beneficial cascades of neurologic occurrence as with the oscillating use of the DEVICE-user interaction. The additional proposed benefits of utilizing and/or stimulating the user's nervous system for perpetuating relief of discomfort as well as actively strengthening the body of the user is a highly beneficial result of a use or uses of the DEVICE.

SUMMARY

An improved positioning device, the DEVICE consists of at least one concave angulated surface, at least one base surface, at least two side surfaces that are substantially parallel to each other, and at least two other side surfaces that are substantially parallel to each other, a concave angulated dihedral valley or essentially dihedral overall shape comprised of at least one concave angulated surface may function, among other things, as a DEVICE which includes multiple embodiments of designs, component materials, various densities of the materials, combinations of materials, functions, interactions, methods of use, densities, and/or combinations of these embodiments to which can be, but not limited to, positioned against, under, supported, braced, utilized, interacted with, and/or behind various parts of the user's body to assist and improve the function of, but not limited to, those areas when the person is, among other things, supine, prone, seated, side lying, adopting a posture, moving, locomoting, sleeping, resting, stretching, supporting, bracing, rehabilitating, positioning, massaging, kneading, scratching, exercising, and/or standing.

The DEVICE is, among other things, differentiated from foam rollers, physioballs, other "body roller" positioning devices, other spinal health equipment, and/or fitness devices including the "Performance Block™" because the DEVICE has, among other things, a distinctive concave angulated dihedral valley shaped user interaction surface which better and uniquely supports actions such as exercises, stretches aspects of the user's muscles, tendons, ligaments, distracts joints, distracts and/or tractions various body parts such as the spine, vertebral discs, joint capsules, nerves, non-pain-producing mechanoreceptors, nerve endings, neurologic tissues, synovial tissues, scar tissue, adhesions, body articular surfaces, bodily tissues, and/or bodily fluids relative to use of the DEVICE, as well as possibly helping the adjoining body regions, directly and/or indirectly, with the areas it interacts with. Additionally, some embodiments of the device are internally structured with layers and/or laminated layers, thus, making improving the DEVICE's supportive nature and comfort more viable especially than single molded devices. The base surface is designed to be positioned in a stable manner from which the DEVICE is thus, among other things, used by or against the user in conjunction with other uses described and/or not described in this application.

The above summary is intended to illustrate exemplary embodiments of the invention, which will be best understood in conjunction with the detailed description to follow, and are not intended to limit the scope of the invention.

PRIOR ART

US Patent application US 2017/0020773 A1 titled "Massage roller" discloses a massage apparatus includes at least one roller. The roller includes a tubular frame, raised rolling bands, and a plurality of massaging protuberances, wherein the height of the bands is at least the height of the protuberances. The bands and protuberances may be flexible and pliable, and made from rubber, silicone, neoprene or foam. A removable cap may be provided.

U.S. Pat. No. 9,463,136 B2 titled HEATABLE MASSAGE ROLLER AND POSTURE AID A massage roller has a central spinal recess portion, a circular wall portion on each side of the spinal recess portion, and an outer portion extending outwardly from each of the circular wall portions, the outer portion having a first diameter at or near the circular wall portion, and a second diameter remote from the circular wall portion, the second diameter being larger than the first diameter.

US Patent application US20110152035 titled "Foam roller exercise device" discloses a foam roller exercise apparatus having first and second portions. The first portion may have a uniform cross-sectional shape, a first curved outer surface having a first radius of curvature, and a second curved outer surface spaced from the first curved outer surface and having a second radius of curvature. The second portion may be separable from the first portion and may have a uniform cross-sectional shape complementary to the first portion.

Chinese patent reference CN 203043430 titled "All-Round Abdominal Exercise Machine Supine Board" discloses an all-round abdominal exercise machine supine board which comprises a rear support, a front support, a seat cushion, a backrest supporting frame and a backrest foam roller arranged on the backrest supporting frame. The all-round abdominal exercise machine supine board is novel in design and has both a supine board function and an abdominal exercise machine function, when supine movement is carried out, fixing bolts are pulled up, a backrest is tightly attached to the back to move together, when leaning-back movement is carried out, a limiting elastic connecting piece plays a role in damping, when a user sits up, the limiting elastic connecting piece plays a role in boosting, the abdominal exercise machine function is achieved, and when different adjusting holes where the fixing bolts are inserted in are located and fixed, the all-round abdominal exercise machine supine board has the supine board function.

U.S. Pat. No. 7,137,926 titled "Foam Roller" describes the exterior of an elongated exercise roller formed of a compressible, foam material, which instead of being cylindrical, has a portion that has a gentler curvature which makes balancing easier.

Patent application WO 2013001314 titled "Physical Exercise Apparatus" discloses a physical exercise apparatus comprising a hollow cylindrical device having first and second end regions, said first and second end regions being closable with closure means, at least one closure means being removable from the respective end region.

US Patent Application US 20120322633 entitled "Exercise roller with resistance bands" discloses an exercise apparatus includes a body roller and at least one resistance band. The body roller includes an interior channel. The resistance band passes through the interior channel of the body roller. Ends of the resistance band extend outward on each side of the body roller. The body roller facilitates applied pressure to a user's body. The resistance bands facilitate resistance training exercises by the user. The body roller provides a structural support for the resistance bands during the resistance training exercises.

US Patent Application US 20110300995 entitled "Exercise roller" discloses an exercise roller comprises of at least two sub exercise roller units, the sub exercise roller units connected together to form a single exercise roller and separable to be usable as separate exercise rollers.

US Patent Application US 20130130872 entitled "Multi-Use Range of Motion Roller" discloses a multi-use range of motion roller that combines the traditional benefits of a foam roller with the added benefits of strength and resistance training.

US Patent Application US 20120071306 entitled "Portable Multipurpose Whole Body Exercise Device" discloses a portable multipurpose whole body exercise device which can be used for general fitness, Pilates-type, core strengthening, therapeutic, and rehabilitative exercises as well as stretching and physical therapy and which includes storable accessories that can be withdrawn from storage within the device and subsequently secured to the main tubular portion of the apparatus.

Many exercise devices are used to improve balance and thus core strength. The "BOSU" is one example. It has a hard, flat, rubberized side and an inflated dome on the opposite side. The user may stand on either side of the BOSU and balance. People also sit on the dome side and perform abdominal exercises. In another exercise, users mount the dome side down and perform balancing push ups with their hands on the flat side. "Wobble boards" and similar devices also improve balance. They have a flat board mounted on a narrow block or roller, and the user balances the board above the block. The "Core Board" is a platform mounted on a base. The mounting allows the platform to tilt to all angles and directions. The platform also can pivot about the base. The mounting is resilient so that the platform returns to its original position when no force acts on it. The device is said to be active with dynamic response to movement. These devices do not have a more direct physical interaction and thus action on the spine-pelvic-hip regions specifically as does the DEVICE's potential use when the user lays themselves on the DEVICE and performs exercises. Thus, the DEVICE encompasses uniquely different designs and functions than these traditional approaches.

"Foam rollers" are another type of device used to facilitate a variety of exercises and stretches, including abdominal, back, quad, shoulders, chest, and other body parts. They vary in size, but they typically are cylindrical or a half round shape of various sizes. Alternatively, the user lies on the roller with the roller axis aligned with the spine. The diameter of the foam roller raises the person's shoulders and back above the floor or mat and forces him or her to balance or stretch or rub against their body. Depending on the person's height, the roller's length is often long enough to support the head and still extend to the hips. From the supine position, the user can perform abdominal crunches, leg lifts, and arm, chest and other exercises. They can also lay on the foam roller with the thighs or other body parts and roll on it to rub out their muscles.

Foam rollers can be uncomfortable or pain provoking when placed beneath the spine in the supine position, for several reasons. Specifically, the height difference between the resting lumbar lordosis of the spinal vertebrae which are lifted several inches off the floor by the thick diameter of the foam roller produces a hyperlordotic force which exceeds the passive normal range of motion of extension of most people's spines. Additionally, the level horizontal orientation of foam rollers, regardless of their textured surface, produce excessive force on the spinal column. Finally, foam roller density, despite the availability of models of different density, is too dense to allow for comfortable use against the spine.

The DEVICE is different in basic function from foam rollers, and/or foam pads, and/or domed devices, and/or ball shaped devices, and/or wobble boards in at least several ways:

a.) The DEVICE's shape incorporates a concave angular edge with substantially flat surfaces that come in interaction with the user resulting in a stable platform for performing exercises or stretches that, when the device is placed properly, by contrast with Wobble boards the device does not require a specific balancing action by the user. While a foam rollers, foam pads, domed fitness devices, and/or spherical fitness devices are primarily cylindrical and/or half round and/or domed and/or spherical in nature and all are a variation of convex curved surface(s) that can specifically elicit a significant balancing, repositioning, or supportive action by the user over those convex surfaces. The DEVICE, by contrast, allows for a direct and significant connection with the user's body which results in the ability to use the DEVICE against a concave surface. Because of this, among other things, in some embodiments a use of the DEVICE significantly closes the kinetic chain for core, hip, and/or other exercises in a new and better way. The DEVICE's user interaction can do so because of the relatively significant, unique, and improved anatomically responsive shape of the DEVICE for health and fitness purposes as compared to the use of a cylindrical or partially cylindrical, a convex user contact composite surface, a spherical, a rounded, and/or a domed health and fitness device.

b.) The DEVICE places the spine and pelvis in unique configurations that support increased range of motions in the spine, intervertebral discs, as well as the pelvis and hips when it is placed under and/or against those areas with the user in a supine, prone, or side lying position. The DEVICE's concave angulated user contact composite surface does so by reducing inordinate pressure directly on the spine, spinous processes, ribs, sacrum, extremities, and/or pelvic-hips because the primary surface that contacts the user is a concave angulated surface. The DEVICE does so without lying flat or horizontally across the contacting surface like foam rollers, yoga blocks, and/or traditional spinal horizontal extension fulcrums.

c.) While foam rollers are available in a variety of densities, surface textures, and materials, they are typically cylindrical or half round more uniform structures, while in some embodiments of the DEVICE, the DEVICE is uniquely constructed of multiple laminated layers in an orientated arrangement. These unique laminated constructions result in a firm supportive device, which in some embodiments, do so while also using a much softer material than foam rollers. This construction makes the DEVICE more comfortable to lay on because the edges easily conform to the users' habitus. The angulated surfaces of the DEVICE also penetrate into areas like the deep gluteal and other concave areas of the body, whereas devices such as foam rollers, cylindrical, rounded, and/or spherical devices although they may have various textures or ridges, cannot penetrate into these concave areas as effectively as the DEVICE.

d). The essentially flat aspect of the concave angulated surface also holds the tissue volume during use which allows the entire volume to be continually interacted with during use whereas a foam roller simply compresses a singular area of tangential interaction then rolls off of it during use or just continues to compress it during use.

e.) In some embodiments of the DEVICE, the DEVICE is uniquely constructed of multiple laminated layers in an orientated arrangement. This unique laminated construction results in a firm supportive device. This construction makes the DEVICE more comfortable to lay on because the edges easily conform to the users' habitus. The angulated surfaces of the DEVICE also penetrate into areas like the deep gluteal and other concave areas of the body, whereas essentially flat devices like a foam pad, although they may have various textures or ridges, cannot penetrate into these concave areas as effectively. The essentially flat aspect of the angulated surface also holds the tissue volume during use which allows the entire volume to be continually interacted with during use whereas a foam pad simply compresses a singular area of tangential interaction to compress during use. This is different than with foam rollers and/or "foam pads" which are another type of device used to facilitate a variety of exercises and stretches, including abdominal, back, quad, shoulders, chest, and other body parts. They vary in size and shape. Many foam pads are typically wedge shaped and convex in nature, whether angulated or rounded on the user's interacting surface. Some foam pads can be uncomfortable or pain provoking when placed beneath the spine in the supine position, for several reasons. Specifically, the height difference between the resting lumbar lordosis of the spinal vertebrae and the altered height of the lumbar lordosis which are lifted several inches off the floor by the thick diameter of the convex foam pad produces a hyperlordotic force which routinely exceeds the passive normal range of motion of extension of most people's spines. Additionally, in comparison with the DEVICE, the more level, horizontal, rounded convex, rounded angulated convex, rounded convex angulated, and/or rounded concave orientation of some foam pads, rollers, and/or rounded devices, regardless of their textured and/or padded surfaces, are more likely to produce an excessive and/or painful interaction force on the user's tissues, spinal column, and/or extremities than the DEVICE. These types of foam pads are often used in fitness settings, rehabilitation facilities, healthcare facilities, private use, gymnastics, and other athletic forms for increasing the user's range of motion. While foam pads are available in a variety of densities, surface textures, and materials, many tend to be more uniform in their structures, thus, similar to the above description.

The Performance Block™ by OPTP contains a patented "dip" which makes it unique. In the OPTP 2019 catalogue the Performance Block™ states: "The versatile foam exercise assistant is ideal for use in yoga, Pilates, physical therapy, and functional fitness. Its supportive nature and patented "dip" make it unique from other yoga blocks. Fitness enthusiasts, patients, trainers, and athletes can all benefit from its distinct shape which allows for creative, challenging movements." "Patented contour design fits the body." Yoga blocks in general are rectangular brick shaped, typically foam, supports for yoga and various exercise and stretching purposes. These yoga blocks are also contrasted with the DEVICE for the same reasons and our response below includes differences for these other yoga blocks as well as the Performance Block as the Performance Block claims differentiation form yoga blocks as part of its patented uniqueness.

The DEVICE is different in basic function from the Performance Block™ by OPTP in many ways including: The DEVICE shape includes a concave angular edge with flat surfaces resulting in a stable platform for performing exercises or stretches that supports the body and diffuses the weight of the load away from the body part contacting the support because it does not specifically wrap around or "fit the body" with in a confined contoured manner like the curved concave "dip" in the Performance Block™. The DEVICE's design difference is uniquely advantageous for having persons of significantly different body shapes, widths, and weights use the DEVICE's flat and concave angular edge's interaction surface. A concave angular edge's flat surface of interaction with the user allows for more variation of a wide range of body widths of the user without the Performance Block's dimensions and shape causing a wrapping constrictive interaction around the low back, pelvis, and ribs inherent to the set dimensions of the curved "dip" of the Performance Block.

Yoga blocks are a large category of brick shaped supports, generally made of foam, and which are widely used for supporting the skeleton and muscles for exercises and stretches both within the yoga environment as well as health and wellness in general. The DEVICE is different in basic function from brick shaped yoga blocks or the curved concave "dip" of the Performance Block in many ways including:

a.) The DEVICE's shape incorporates at least one concave angular edge with essentially flat surfaces resulting in a stable platform for performing exercises or stretches that supports the body and diffuses the weight of the load away from the interaction support because it does not specifically wrap around the body in a set contoured manner like the curved concave "dip" in the Performance Block™.

b.) This design difference is uniquely advantageous for having persons of significantly different body shapes, widths, and weights use the DEVICE's flat and concave angular edge's interaction surface. A concave angular edge's flat surface of interaction with the user allows for more variation of a wide range of body widths of the user without causing a wrapping constrictive interaction inherent to the set dimensions of the curved concave "dip" of the Performance Block.

Unlike the Performance Block™, "Yoga blocks," and the like, in at least one embodiment of the DEVICE, FIG. 5, angle 23 may incorporate an approximate 73 degree angle aspect which is possibly for comfort, relief from discomfort, for providing support to maximize effectiveness of the user's position and/or method of use. Some smaller more horizontal angles may tend to promote the device to impinge excessively upon the back or other body regions being supported; while some larger or deeper concave angles may result in insufficient support for the device to be fit for purpose. While early versions of the DEVICE utilized angles in this range further development of the DEVICE's uses has become apparent and requires the wide range of dimensions to be maintained for the resulting embodiments to be more fit for purpose than the one referenced here, for example obese individuals as well as elite athletes and more, and the performance of the user and DEVICE may vary with the angle and dimensional deviations. For these reasons other embodiments of the DEVICE include various material, densities, structural arrangements, angles, and/or combinations to accentuate the best uses of those embodiments.

An example of this is seen in FIG. 4 which contains multiple laminated layers and/or sectioned layers of various widths, in this embodiment eight laminated sectioned layers numbered 13-20, which can provide greater overall support to loads placed against it over the entire surface of a concave angulated surface while maintaining a relative soft material presentation of the individual laminated layers and/or sectioned layers to provide a soft interaction with the user at the edges that come into interaction with the user. The laminated layers and/or sectioned layers and/or laminated sections offer a great advantage for the DEVICE to provide multiple embodiments which may be available in, but not limited to, a variety of densities, surface textures, and materials of the DEVICE.

BENEFITS OF THE DEVICE

The DEVICE consists of an essentially simple overall design that incorporates many variations of manufacturing and design ranges and provides a significant benefit to the user for spinal care as well as the neuromusculoskeletal system, circulatory system, and/or lymphatic system as a whole, especially when used as described and progressions of the methods described and in this document.

When the DEVICE is, at least, placed under the spine of the supine person, it delivers an extension force into any portion of the spine, lumbosacral junction, lumbopelvic, pelvo-femoroacetabular joints, the knee joints, the extremity joints, and/or cervicobrachial regions. The DEVICE also may assist as, but not limited to, a fulcrum, lever, and/or be capable of uniquely dispersing a load during the interaction between the user and the DEVICE neuromusculoskeletal actions, both directly and/or indirectly, relative to these joints' as well as functions of the related neuromusculoskeletal structures. Furthermore, the DEVICE may function as a fulcrum, lever, and/or be capable of uniquely dispersing a load during the interaction between the user and the DEVICE surface against which the user may move their body against the DEVICE and/or also use the DEVICE to move against their body in, among other things, a rubbing, kneading, scratching, and/or massaging like oscillating motion similar to that of rubbing and/or massaging an infant to induce calming or sleep.

In this disclosure, the term "proximal" refers to the portion of a structure closer to a user, while the term "distal" refers to the portion of the same structure further from the user. As used herein, the term "user" refers to vertebrate animals, primarily humans, but in some embodiments humans may use the device for pet and/or animal care. In some embodiments, the device is, among other things, used by a pet or animal as, but not limited to, a pet scratcher. In some embodiments, the terms "clinician" or "healthcare provider" refer to a doctor, physician, nurse, physical therapist, chiropractor, athletic trainer, or other care provider, and may include support personnel. The terms "generally," "substantially," and "about" shall be understood as words of approximation that take into account relatively little to no variation in the modified term(s) (e.g., differing by less than 10%). Additionally, in the drawings and in the description that follows, terms such as upper, lower, top, bottom, front, rear, right, left, and similar directional terms are used simply for convenience of description and are not intended to limit the disclosure.

The primary actions of the DEVICE are related to the neuromusculoskeletal system, circulatory system, and/or lymphatic system to help improve their functioning by action initiated with a use of the DEVICE. These also include, but are not limited to, those actions related to an activity promoting at least one of passive spinal intervertebral disc decompression, active spinal intervertebral disc decompression, passive spinal intervertebral disc flexion distraction, active spinal intervertebral disc flexion distraction, passive spinal intervertebral disc extension distraction, active spinal intervertebral disc extension distraction, the spinal disc pump, spinal intervertebral disc imbibition, spinal intervertebral disc repair, spinal intervertebral disc hydration, spinal intervertebral disc inflammation reduction, spinal intervertebral disc debris reduction, spinal joint anatomic effects, spinal joint physiologic effects, spinal traction, extremity joint anatomic effects, extremity joint physiologic effects, joint decompression, joint hydration, joint repair, joint distraction, joint traction, muscle repair, muscle stretching, muscle elongation, muscle strengthening, muscle relaxation, muscle spasm relaxation, tendon repair, tendon stretching, tendon strengthening, ligament repair, ligament strengthening, ligament stretching, cartilage repair, cartilage hydration, disrupting scar tissue, disrupting the formation of scar tissue, elongating scar tissue, elongating neurological tissues, decreasing fluid accumulation, improving fluid drainage, improving circulation, improving lactic acid equilibrium, improving lymphatic flow, improve tissue drainage, or improving tissue elasticity of the user.

Furthermore, including that the activity comprising of, among other things, at least one of passive, active, or isometric movements by the user: the method of use of the DEVICE further includes, but not limited to, the activity comprising of at least one of: stimulating proprioceptors, stimulating non-pain-producing mechanoreceptors, stimulating nociceptors, or stimulating the vestibular system. The activity also includes stimulating at least one of, but not limited to: afferent impulses from the periphery to the central nervous system, neurological tissue, the release of endorphins, the descending inhibitory pathways, the subsequent depression and/or inhibition of contractile tissues, the subsequent depression and/or inhibition of pain promoting tissues, the subsequent sense of relaxation of the body, the subsequent sense of relaxation of the mind, the subsequent sense of relaxation of the spirit, or the subsequent sense of relaxation of the soul of the user. Furthermore including that the activity comprises of at least one of tissue repair, healing, physiologic equilibrium, a beneficial mental state, a beneficial emotional state, a state of relaxation, improved neuromusculoskeletal system, improved circulatory system, improved lymphatic system, a beneficial energetic state, proposed proper spinal disc pump imbibition action which is at least beneficial to allow for proper healing but not limited to at least one of after disc injury, overloading, immobility, decreased range of motion, mechanical damage, wear and tear, hypomobility, hypermobility, reduced disc failure properties, altered cell level signals, matrix remodeling, incomplete healing, reduced motion segment function, pain, or degenerative changes.

Additional actions of the DEVICE are related to, at least one of, but not limited to, all specific anatomical areas of the bodily regions subjected to a use of the DEVICE as well as any possible improved range of motion (ROM) of these and/or other neuromusculoskeletal tissues not specifically subjected to a use of the DEVICE which may include the spine, pelvis, lumbosacral, lumbopelvic region, midsection, core neuromusculoskeletal tissues, IT Band(s), hip(s), lower extremity(ies), upper extremity(ies), trunk, cervical spine, cervicobrachial region, cervicocranial region, head, jaw, and/or shoulders; furthermore, the joints and their contents may encompass the ligaments, joint capsule, all articular surfaces including their tissues and fluids, surrounding tendons, muscles, synovial tissues, lymphatic system, circulatory system, and/or vascular system that are effected by a use of the DEVICE.

Other actions of the spine that are potentially improved by a use of the DEVICE may include, but are not limited to: the priming, restarting, facilitating, repairing, and improving the "spinal disc pump," or intervertebral disc (disc) imbibition process, which occurs throughout the spine and more specifically in the lumbosacral, lumbar, thoracolumbar, thoracic, cervicothoracic, thoracic, cervical regions depending on the positioning of the DEVICE. The spinal disc pump is an unconscious normal healthy physiologic movement pattern involving, at least, the spinal intervertebral disc action of imbibition as an osmotic exchange system within the spine, the intervertebral discs and their motor units, which occurs when a person is non-weight bearing and/or when an additional load is removed from the disc during a mechanical unloading action which may occur during, at least one of, the methods of use of, but not limited to, the described embodiments of the DEVICE in this application. The disc pump is a spinal motion that encourages and/or creates a pumping motion and/or osmotic exchange action of fluids within the, at least but not limited to, spinal discs and/or intervertebral motor units into distraction, extension, and/or flexion. This spinal disc pump action is proposed to perpetuate normal imbibition and resorption of water and nutrient content into the disc, increases such water and nutrient content flow, and/or furthers the beneficial exchange of fluids, and nutrients into and out of the disc as well. This physiologically proposed normal spinal disc pump imbibition action is proposed to be needed to allow for proper healing for at least one of, but not limited to, after disc injury, overloading, immobility, hypermobility, decreased range of motion, mechanical damage, wear and tear, hypomobility, hypermobility, reduced disc failure properties, altered cell level signals, matrix remodeling, incomplete healing, reduced motion segment function, pain, and degenerative changes. The DEVICE is proposed to appreciably benefit the spinal disc pump and imbibition of a person's physiology.

Additional actions of the DEVICE include, but are not limited to, dispersing and distributing the load experienced by a person who wears a pack on the body by moving the pack's position from its original position against the body of the wearer to make the load more comfortable for the wearer by applying a possible fulcrum, lever, and/or be capable of uniquely dispersing a load during the interaction between the user and the DEVICE as a possible cushion support system and/or that uniquely distributes the forces from the load in a better way for user comfort and/or support as well as limits possible inhibiting of the breathing mechanisms and/or other bodily functions of the user as compared with wrapping, supporting and/or bracing the user with a curvilinear and/or cylindrical interaction surfaces.

The DEVICE can also serve as, but not limited to, a unique spinal, lumbar, lumbopelvic, hip, back fulcrum, back brace, back cushion, and/or cushion support for any type of backpack or weighted backpack system. Such devices may include military backpacks, school book backpacks, athletic hydration backpacks, oxygen tanks, air supply packs, other gaseous supply tanks, canisters, and/or beverage packs that are positioned on and/or carried by a user.

Furthermore, other users include, but not limited to: firefighters, emergency personnel, patients with air supply requirements as well as wherein the device is, among other things, positioned to allow the user to undergo at least one activity of, but not limited to, stretching, supporting, bracing, rehabilitating, positioning, massaging, kneading, scratching, exercising, psoas muscle exercising, psoas muscle stretching, psoas muscle repairing, iliopsoas muscle exercising, iliopsoas muscle stretching, iliopsoas muscle repairing, shoulder exercises, shoulder stretches, rotator cuff exercises, rotator cuff stretches, elbow exercises, elbow stretches, wrist exercises, wrist stretches, hand exercises, hand stretches, finger exercises, finger stretches, hip exercises, hip stretches, knee exercises, knee stretches, ankle exercises, ankle stretches, foot exercises, foot stretches, plantar fascia exercises, plantar fascia stretches, toe exercises, toe stretches, pelvic tilting, core exercises, pelvic tilting from core muscular activity, chin retractions, spinal exercises, spinal stretches, spinal decompression, spinal traction, spinal range of motion improvement, extremity exercises, extremity stretches, extremity joint stretches, extremity joint distraction, extremity joint labral decompression, extremity joint exercises, extremity joint traction, extremity joint range of motion improvement, supporting, positioning, gliding, oscillating, rubbing, sliding, rolling, rocking, wobbling, sitting, reclining, lying, walking, running, hiking, backpacking, carrying a travel pack, wearing a fanny pack, carrying a child carrier, carrying a pet carrier, carrying a mail carrier's pack, carrying a backpack, carrying a firefighter's pack, carrying a military field pack, carrying a military pack, carrying a rucksack, carrying a military weapon, wielding a military weapon, wielding a weapon, carrying a weapon, carrying furniture, carrying appliances, carrying equipment, carrying a scuba pack, scuba diving, riding a motorcycle, biking, bicycling, tricycling, piloting, driving, massaging, kneading body tissues, sleeping, meditating, performing yoga, performing a sex act, performing thi chi, resting, kite surfing, surfboarding, windsurfing, parasailing, parachuting, firefighting, balancing, strengthening, rowing, using an ergometer, using a harness to transfer a person, using a harness to transfer a patient, using a rowing machine, rowing a boat, rowing a scull, kayaking, or exercising. The device is, among other things, also used as at least one of a pet care device, an animal care device, veterinary animal care device, an animal self-rubbing device, or mounted animal self-rubbing device.

The DEVICE can be incorporated during production and/or fitted as an add on to a surface of these carrying devices and/or other apparatus which press against the user's back, waist, pelvis, hips, extremities, chest, head, body, and/or shoulders. The shape of the DEVICE also allows for the ribs to continue to maintain their bucket handle motion which includes expansion and constriction with normal and exertional breathing. This concave angulated user contact composite surface design is superior to a rounded and/or curved concave back support and/or a back support that wraps around the curvature of the wearer's back because this wrapping apparatus can confine the expansion of the rib cage's motion with such breathing especially when exertional. a concave angulated aspect of the DEVICE allows the rib angles to pivot on the flat surface thus not or minimally restricting expansion and other normal and exertional breathing patterns when wearing a backpack. In contrast, a merely curved concave support or fitted wrap would offer lateral restriction to the expanding ribs, thus interfering and restricting the ability of the wearer to breathe. The DEVICE is engineered and designed to allow both normal and exertional breathing to occur over the pivot points of the rib angles against the DEVICE's concave angulated shape.

The DEVICE can be manufactured with different heights and/or other dimensions, to better accommodate different sized bodies, various uses, various methods of use, and also to provide different variations in flexibility of use from one user to another. The DEVICE can be manufactured with different materials, but in our experience, but not limited to, closed cell foam provides an optimum mix of both support and softness against the body. The materials which may be able to comprise the device include but not limited to are at least one of: foam, graphite, fiberglass, composite, gel, water, air, gas, fiber, plastic, microfiber, metal, sand, glass, ceramic, stone, metallic, polymer, resin, paper, cloth, wood, polycarbonate, silicone, rubber, wax, carbon fiber, Teflon, polyester, polymer, kevlar, dacron, water-resistant material, waterproof material, oil-resistant material, oil proof material, or organic material.

The uses of the DEVICE also include being used as a body support that increases and reduces resistance to pelvic tilting and flexing and distraction of the lumbosacral junction, lumbopelvic, and thoracolumbar junction in general by placing the DEVICE under the supine pelvis in a manner to assist these motions.

The uses of the DEVICE also include being used as a body support that increases, and reduces resistance to, hip extension when used with the user supine and flexing and distraction of the lumbosacral junction and lumbopelvic in general by placing the DEVICE under the distal pelvis and femoral acetabular (FA) joint(s) in a manner to assist these motions.

The uses of the DEVICE also include acting as a lumbosacral and lumbopelvic support for the seated user. The DEVICE can be placed behind the lumbosacral and lumbopelvic areas in a comfortable fashion to assist in maintaining proper support for the lumbar lordosis, lumbosacral lordosis, lumbopelvic lordotic positions, and thoracolumbar positions, and assisting in maintaining an upright cervicothoracic posture and helping to mitigate a thoracic hyperkyphosis and forward head carriage. The proposed more supported posture encouraged by at least one of the many uses of or at least a use of the DEVICE decreases physical stress on the spinal intervertebral discs and the spinal motor units as well as with respect to their surrounding neuromusculoskeletal system, circulatory system, and/or lymphatic system.

The uses of the DEVICE also include a supportive platform for various body weight exercises, weight-lifting exercises and/or exercises that include added resistance.

The uses of the DEVICE also include being used as a body support that increases, and reduces resistance to, elbow and wrist extension when used with the user supine and either passively or actively flexing and distraction the wrist or elbow joint(s) in general by placing the DEVICE under the elbow(s) or wrist(s) in a manner to assist these motions. This could be helpful for a person who had difficulty straightening their elbow by placing the supine elbow over a concave angulated edge of the DEVICE. This placement could allow the DEVICE to hold and maintain a specific supinated or pronated, or a specific combination, forearm and wrist to allow for a proper positioning of the desired stretch and/or exercise, especially when wrist flexion or extension are additionally targeted to be positively effected with improved function along with supination, pronation, circumduction, and combinations there within.

The uses of the DEVICE also include being used as a body support that increases, and reduces resistance to, ankle plantar extension when used with the user supine and under or beneath the ankle generally against the achilles tendon and either passively or actively plantar flexing and dorsi flexing the ankle and/or foot joint(s) and arch(es) in general by placing the DEVICE under and posterior to the ankle(s) or foot (feet) in a manner to assist these motions. This could be helpful for a person who had difficulty straightening their ankle and foot by placing the supine ankle over a concave angulated edge of the DEVICE. This placement could allow the DEVICE to hold and maintain a specific supinated or pronated, or a specific combination, ankle, and ankle and mid and forefoot to allow for a proper positioning of the desired stretch and/or exercise, especially when ankle flexion or extension are additionally targeted to be positively effected with improved function along with the mid and forefoot (feet) eversion, inversion, supination, pronation, circumduction, and combinations there within. The stretch is further accentuated by placing a weight over the distal foot when supine and allowing the weight to help stretch the various soft tissues of the distal lower extremities, ankle, foot, and toes into a plantar motion. This could be highly beneficial for swimmers to improve their streamline position and thus decrease their drag coefficient while swimming. Or, a ballet or other dancer to better point or come up on point by increasing ankle and foot plantar flexion.

The uses of the DEVICE also include a support for strength training, body stretching, spinal stretching, extremity(ies) stretching, for relaxation, general or competitive or elite level physical efforts, physical rehabilitation, meditation, spinal rehabilitation, spinal disc and vertebral motor unit injury recovery and injury prevention, core and abdominal and spinal and hip and lower extremity(ies) and cervical neuromusculoskeletal strengthening.

The uses of the DEVICE also include a support for facilitating pain relief such with body stretching, spinal stretching, extremity(ies) stretching, for relaxation, general or competitive or elite level physical efforts, physical rehabilitation, meditation, spinal rehabilitation, spinal disc and vertebral motor unit injury recovery and injury prevention, core and abdominal and spinal and hip and lower and upper extremity(ies) and cervical neuromusculoskeletal strengthening.

The uses of the DEVICE also include a support for the lower abdomen and upper pelvis with the DEVICE user face down or prone to allow for the flexion and distraction of the spine, cervical, thoracic, lumbar, lumbosacral, and lumbopelvic spine and the associated neuromusculoskeletal system, circulatory system, and/or lymphatic system. This position can also serve as a support for strength training, body stretching, spinal stretching, extremity(ies) stretching, for relaxation, general or competitive or elite level physical efforts as also performed in sports, physical rehabilitation, meditation, spinal rehabilitation, spinal disc and vertebral motor unit injury recovery and injury prevention, core and abdominal and spinal and hip and lower extremity(ies) and cervical neuromusculoskeletal strengthening to these areas and others and tissues of the body.

The uses of the DEVICE also include a support for the waist region including the thoracolumbopelvic spine and/or pelvic-hip region when the user is lying on their side with the DEVICE placed under their waist, hip, or torso. This position can also serve as a support for strength training, body stretching, spinal stretching, extremity(ies) stretching, for relaxation, general or competitive or elite level physical efforts, physical rehabilitation, meditation, spinal rehabilitation, spinal disc and vertebral motor unit injury recovery and prevention, core and abdominal and spinal and hip and lower extremity(ies) and cervical neuromusculoskeletal strengthening to these areas and others and tissues of the body.

The uses of the DEVICE also include a support for the waist region including the thoracolumbopelvic spine and/or pelvic-hip region when the user is lying on their side with the DEVICE placed under their waist, hip, or torso while the user is in bed or resting on a surface. The DEVICE offers support and stability and comfort to this region to help the user's spine and neuromusculoskeletal system not sink or distort onto or into their bedding or resting surface. Some areas of the neuromusculoskeletal system here referenced include the cervicobrachial region, the shoulders, ribs, thoracolumbopelvic and hip regions.

In one embodiment of the DEVICE, but not limited to FIGS. 12, 12a, and 13 the interaction surface, which comprises of a concave angulated surface, is described by the DEVICE having a concave angulated dihedral valley height number 21 substantially equal to the heights of each side surface 4 and 5 creating a concave angulated blade shape. This embodiment's representation of the DEVICE better produces a therapeutic tool as a handheld device for more specific use by a user including a healthcare practitioner, clinician, coach, trainer, and/or personal use. The ability to manufacture and subsequent dimensions of such a concave angulated blade shape are based on the various materials, densities, and/or orientations that are offered in this document. One primary function and method of use of this embodiment could be, but not limited to, a therapeutic DEVICE that is operated by an apparatus, a clinician, healthcare person, and/or a person upon the body of the user receiving the application of the DEVICE. In this embodiment a concave angulated blade aspect of the DEVICE may include it being attached to an apparatus including but not limited to that of a multitool.

BRIEF DESCRIPTION OF THE DRAWINGS

The disclosure will now be made, by way of example, with reference to the accompanying not to scale drawings in which: Any measurements or ranges of measurements in any embodiments that are at least referenced in this application are offered as a general reference for some of the embodiments of the DEVICE detailed in this application, but are not intended to imply any limitation on potential dimensions of the DEVICE.

FIG. 3 is also a perspective view of an illustrative embodiment of the DEVICE (without the vertical laminated sections specifically drawn in which are depicted in FIG. 4). The depth of FIGS. 2, 3, and 4 are not to scale, they are presented here this way to make the multiple layers clear.

FIG. 11a is a front perspective view of an illustrative embodiment of the DEVICE that also demonstrates dihedral laminated layers of the at least two other side surfaces that are substantially parallel to each other 31 and 32 is one of the at least two side surfaces that are substantially parallel to each other relative to 32a which is the another side surface that are substantially parallel to each other. 1 represents the base surface. 21 represents the height of the valley portion of the DEVICE and is incorporated into the at least one concave angulated surface which consists of at least two or more surfaces, 2 and 3, that are connected at the substantially dihedral edge 21a comprising a cradle for a body of a user.

FIG. 11b is a base perspective view of an illustrative embodiment of the DEVICE that also demonstrates dihedral laminated layering of another of at least two other side surfaces that are substantially parallel to each other 31a and 33 represents the intersection of the dihedral laminated layers with base surface 1.

FIGS. 12 and 12a are respectively a perspective view and a bottom view of an illustrative embodiment of the DEVICE that also demonstrates a height variation of the substantially parallel side surfaces 34 and 35, also demonstrates a equal height variation of the substantially parallel side surfaces 34 and 35 which is different from FIG. 11 and may be used as a therapeutic, hand held, pocket, or collapsible device.

FIG. 13 is a perspective view of an illustrative embodiment of the DEVICE that also demonstrates a non closure variation of FIG. 12's substantially equal height variation of the substantially parallel side surfaces 34 and 35.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the claims. Furthermore, there is no intention to be bound by any expressed or implied theory presented in the preceding technical field, background, brief summary of the following detailed description.

Figure 27:
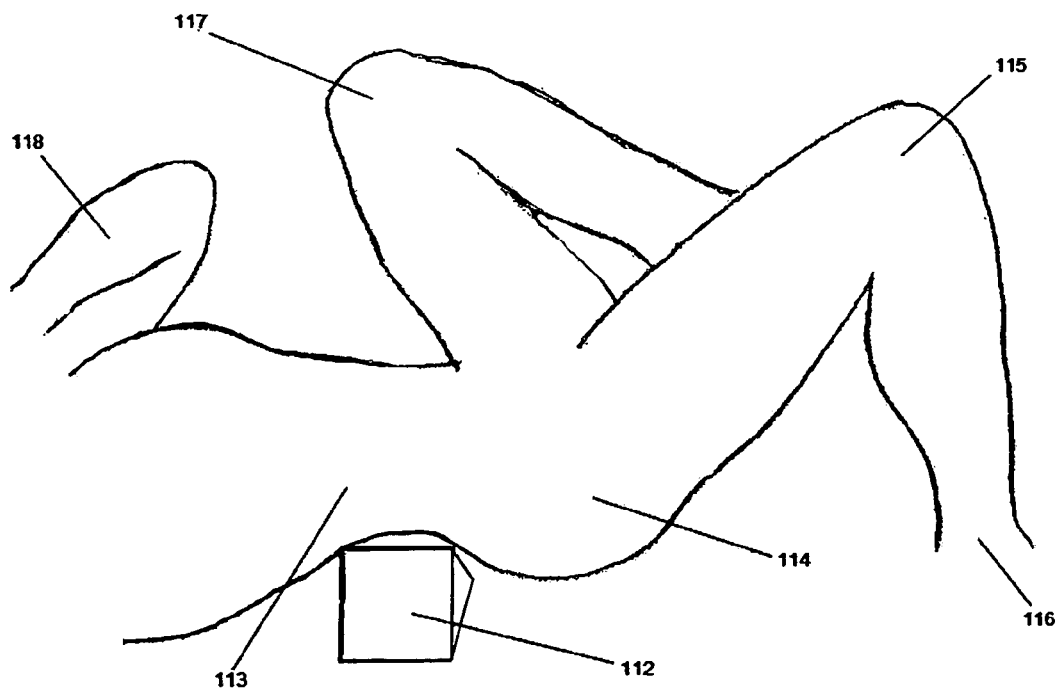
FIG. 27 is a side view of an illustrative embodiment of the DEVICE utilized in a type of core and spine workout in which a user lies on the DEVICE 112 placed against and under the user.
Figure 28:
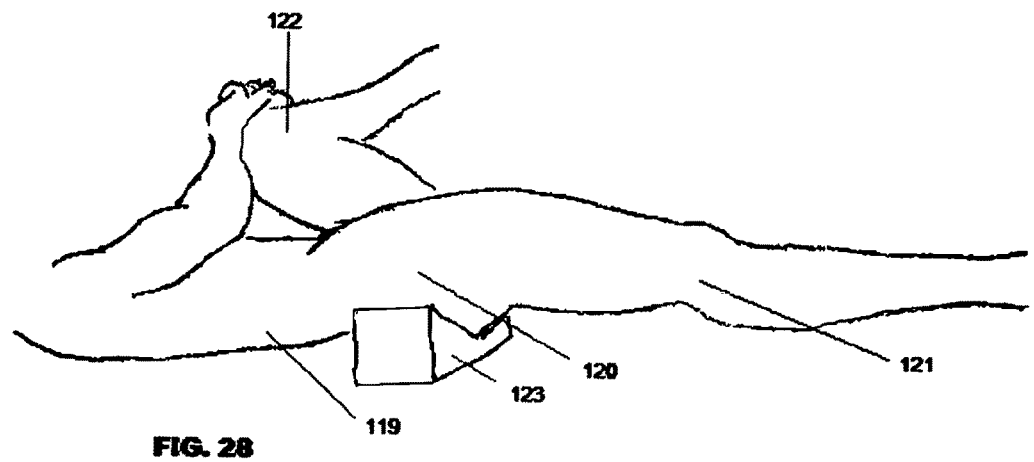
FIG. 28 is a side view of an illustrative embodiment of the DEVICE utilized in a type of core, hip, thigh, and buttocks workout which also can stretch the lower spine 119, pelvis and hips 120 (lumbopelvifemoral region 119-120) when a user lies on the DEVICE 123.
Figure 29:
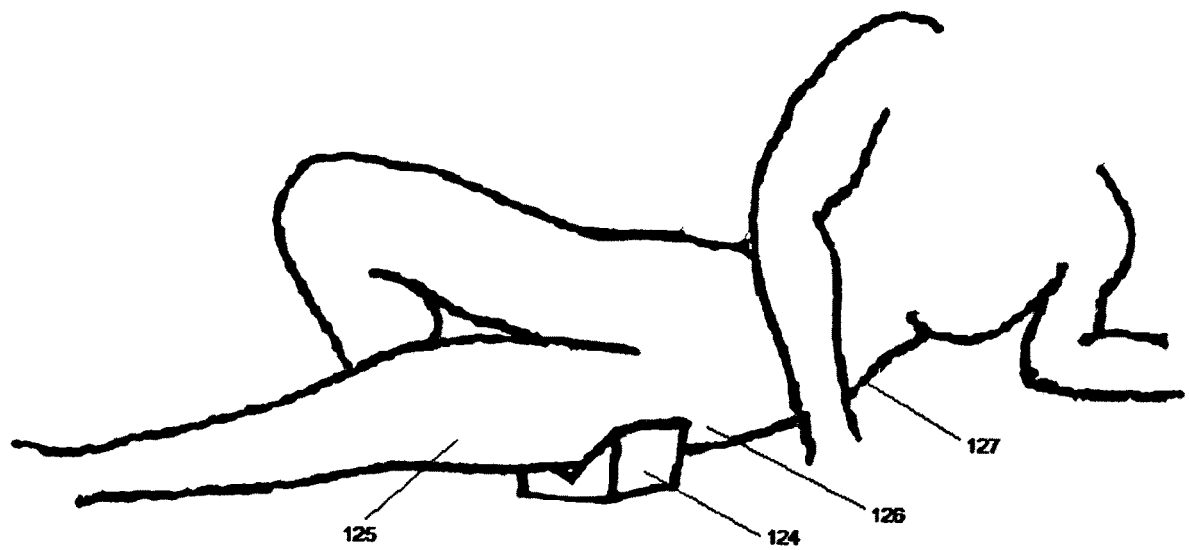
FIG. 29 is a side view of an illustrative embodiment of the DEVICE utilized, among other things, in a type of inner thigh, hip, buttocks, and core workout which also can stretch or strengthen the lower spine 127, pelvis and hips 126 (lumbopelvifemoral region 127, 126, and 125) when a user lies on the DEVICE 124 placed against and under the pelvifemoral region 126 as well as further down the thigh under the IT Band 125 or beyond.

The various embodiments discussed in this application, but not limited to, often describe various orientations that are offered to help produce a different and more desired user interaction based on the physical attributes of the user, as well as the intended use, and/or method of use. FIGS. 27, 28, and 29 help the reader further visualize a few simple examples of operation starting with the user, but not limited to, placing the DEVICE's concave angulated surface against a body part while the base surface functions as a stabilizing platform to provide a more secure user interaction to help perform a use of the DEVICE.

The DEVICE may be placed underneath and/or against whichever part of a body for, but not limited to, at least one of stretching, supporting, bracing, rehabilitating, positioning, massaging, kneading, scratching, or exercising a body of a user. For instance, the DEVICE may be used with the upper region of the spine, the sacrum, the cervical spine, the various regions of the axial skeleton, the appendicular skeleton, the ankle, the elbow, the thoracic spine, the extremities, the torso, the shoulders, the hips, or for a full-body use. For some uses, merely lying supine provides sufficient pressure for stretching the effected body parts encouraging more flexibility and/or an improved functioning position, especially those of extension. Also, when the DEVICE is placed under and/or against the supine user's sacrum and possibly combined with one or both knees being pulled to the chest, the pelvis moves into flexion rather than extension, as does the lumbopelvic region; thus, providing a superior stretching position to that of an non-concave angulated positioning device. This is, among other things, related to the DEVICE'S concavity allowing by providing space for the acceptance of the relative convex angulated anatomy of the posterior aspect of the pelvic innominate bones and protruding sacral curvature to be cradled and not simply pressed against by traditional rounded or cylindrical surfaces regardless of their materials or densities. When lying on the DEVICE the user may also undergo one of an improvement of muscular recovery, responsiveness, relaxation, toning, and/or rehydration.

Figure 1:
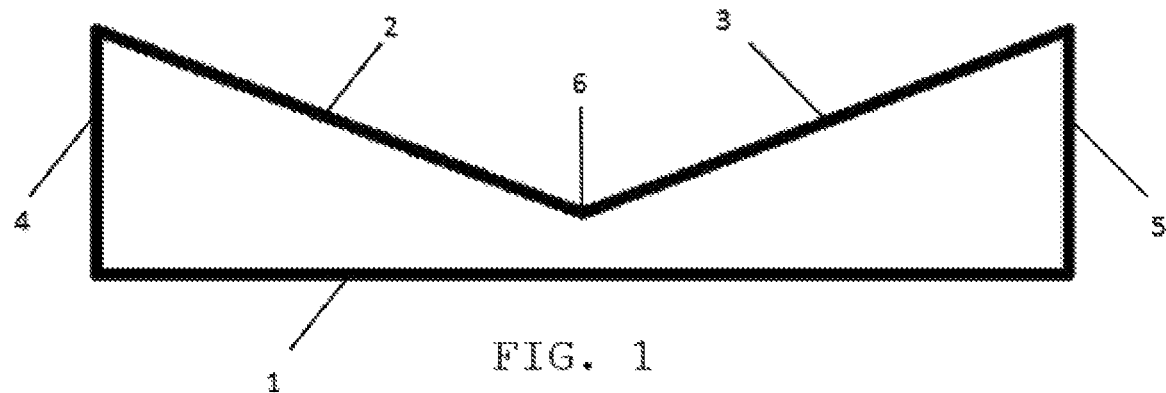
FIG. 1 is a cross-sectional front view of an illustrative embodiment of the DEVICE.

FIG. 1 is a cross-sectional front view of an illustrative embodiment of the DEVICE. The bottom 1 of the DEVICE is considered the base surface and provides stability for a use of the DEVICE. The upper concave angulated dihedral surfaces 2 and 3 are angled upward from concave dihedral angulation edge 6 to a ridge connection with side surfaces 4 and 5. 4 and 5 are the substantially parallel side surfaces of the DEVICE and they are repeated throughout the various embodiments although they may be numbered differently to help better define that embodiment's uniqueness. All angulated surfaces and side surfaces are approximately flat. In this embodiment the base surface 1 is approximately flat.

Figure 2:
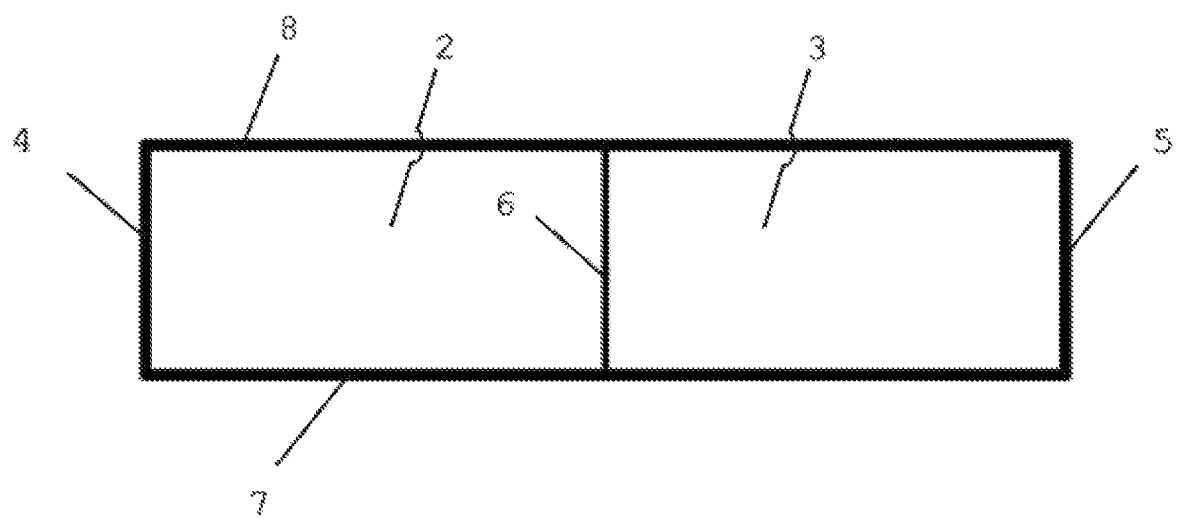
FIG. 2 is a top perspective of an illustrative embodiment of the DEVICE depicted in FIG. 1's embodiment. Demonstrating an embodiment of a concave angulated surface.

FIG. 2 is a top perspective of an illustrative embodiment of the DEVICE depicted in FIG. 1's embodiment. The upper concave angulated surfaces 2 and 3 are angled and meet at concave angulated dihedral valley 6. 4 and 5 are the side surfaces of the DEVICE. 7 and 8 are the long side surfaces of the DEVICE and are substantially parallel to each other. They are also in approximate right angles with the other substantially parallel side surfaces. All surfaces are approximately flat.

Figure 3:
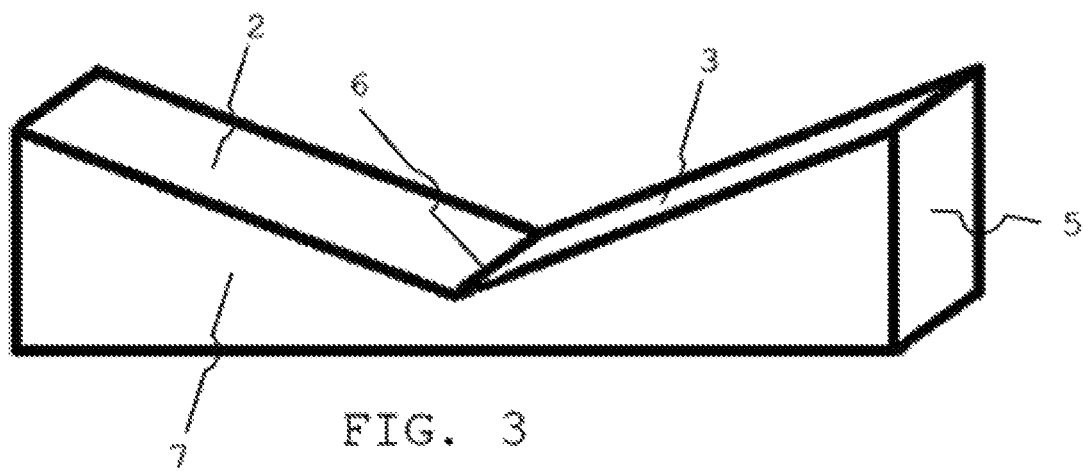
FIG. 3 is a perspective view of an illustrative embodiment of the DEVICE. The upper concave angulated surfaces 2 and 3 are angled and meet at concave angulated dihedral valley 6. 4 (hidden) and 5 are the short side surfaces of this smaller dimensional and more limited embodiment of FIG. 1 and FIG. 2.
Figure 4:
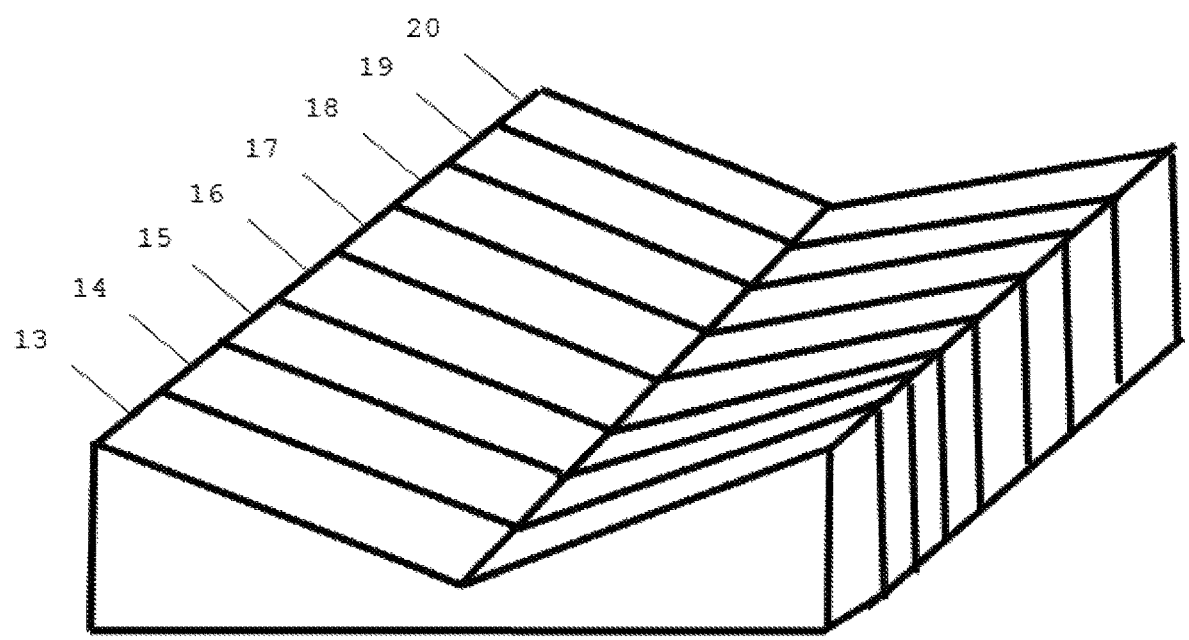
FIG. 4 is a depth perspective view of an illustrative embodiment of the DEVICE composed of eight vertically laminated (i.e connected) layers 13 through 20 are approximately identical and aligned with each other.

FIG. 3 is a perspective view of an illustrative embodiment of the DEVICE. The upper concave angulated surfaces 2 and 3 are angled and meet at concave angulated dihedral valley 6. 4 (hidden) and 5 are the short side surfaces of this smaller dimensional and more limited embodiment of FIG. 1 and FIG. 2. The vertical height of side surfaces 4 and 5 may range in dimensions. 7 is a long side surface of the front or rear side surface of the DEVICE. The vertical distance between concave angulated dihedral valley 6 and bottom 1 ranges as well. The concave angulated dihedral valley 6 is located approximately equidistant from the short side surfaces 4 and 5 of the subsection of the DEVICE. The length of 1 ranges relative to the other dimensions and required uses. The width of a concave angulated dihedral valley 6 (also the depth of the DEVICE) ranges as well. All surfaces are approximately flat. Other embodiments call for much different dimensions as per their more unique use, as with use with obese people, elite athletes, pets, large animals, children, the elderly, and many more uses described in this application. FIG. 3 is also a perspective view of an illustrative embodiment of the DEVICE (without the vertical laminated sections specifically drawn in which are depicted in FIG. 4). The depth of FIGS. 2, 3, and 4 are not to scale, they are presented here this way to make the multiple layers clear.

FIG. 4 is a depth perspective view of an illustrative embodiment of the DEVICE composed of eight vertically laminated (i.e connected) layers 13 through 20 are approximately identical and aligned with each other. Proportions of the subsections to each other are not to scale for the DEVICE which is depicted by the overall dimensions of embodiment depicted in FIG. 3. All surfaces are approximately flat.

Figure 5:
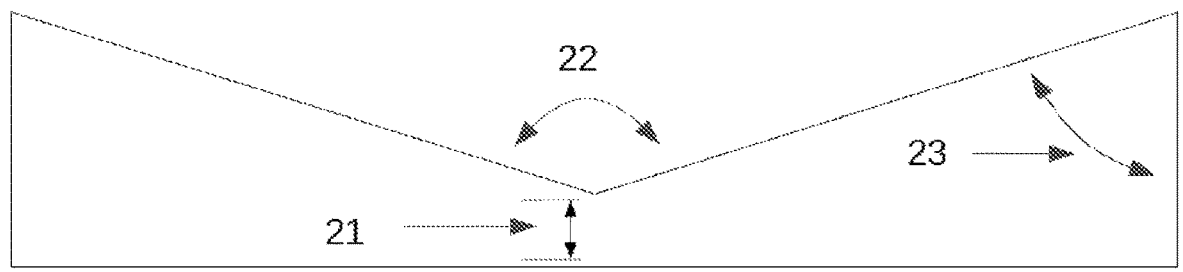
FIG. 5 is a cross-sectional front view of an illustrative embodiment of the DEVICE constructed in accordance with the DEVICE for smaller users and some uses depicting the angles and height 21 of the concave angulated dihedral valley from the base surface 1 from FIG. 1.

FIG. 5 is a cross-sectional front view of an illustrative embodiment of the DEVICE constructed in accordance with the DEVICE for smaller users and some uses depicting the angles and height 21 of the concave angulated dihedral valley from the base surface 1 from FIG. 1. All surfaces are approximately flat.

Figure 6:
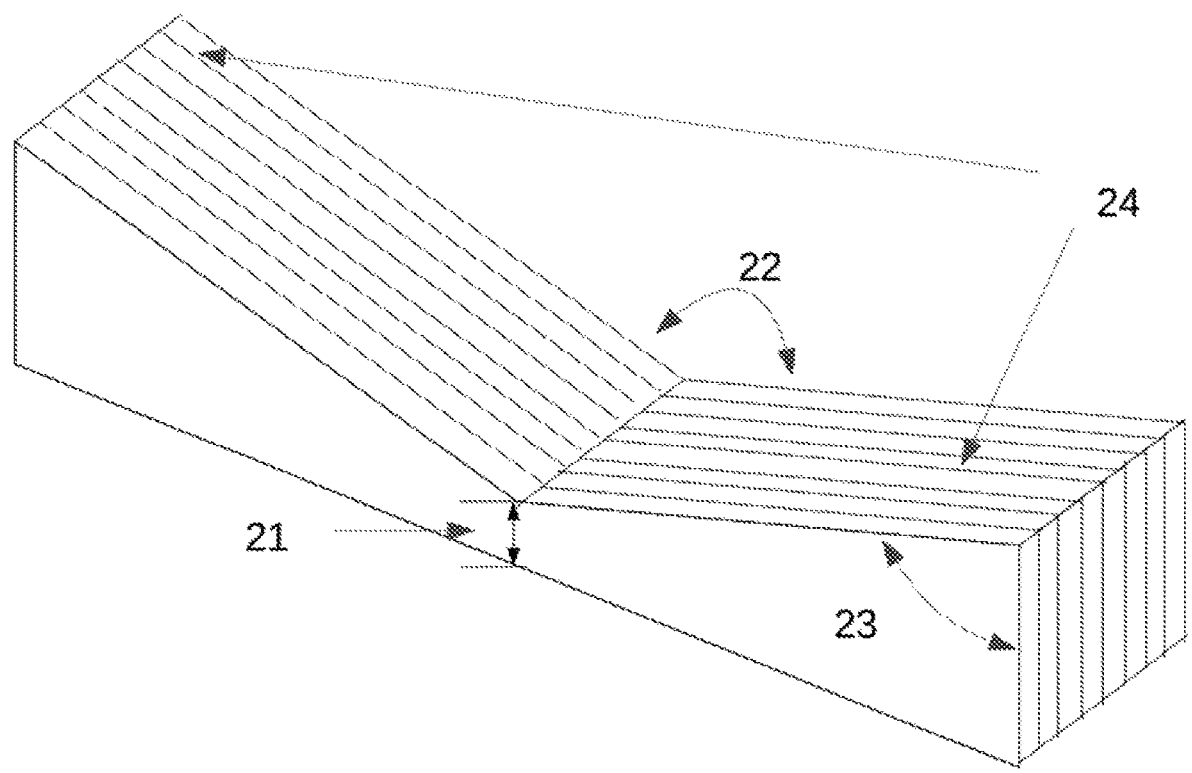
FIG. 6 is a depth expanded perspective view of an illustrative embodiment of the DEVICE and in this embodiment comprises more vertically laminated (i.e connected) layers than other embodiments, depicting the angles 23 and concave angulated dihedral 22 valley height 21.

FIG. 6 is a depth expanded perspective view of an illustrative embodiment of the DEVICE from FIG. 5 frontal view and is composed of eight vertically laminated (i.e connected) layers, depicting the angles 23 and concave angulated dihedral 22 valley height 21. 24 references two concave angulated user surfaces as examples.

Figure 7:
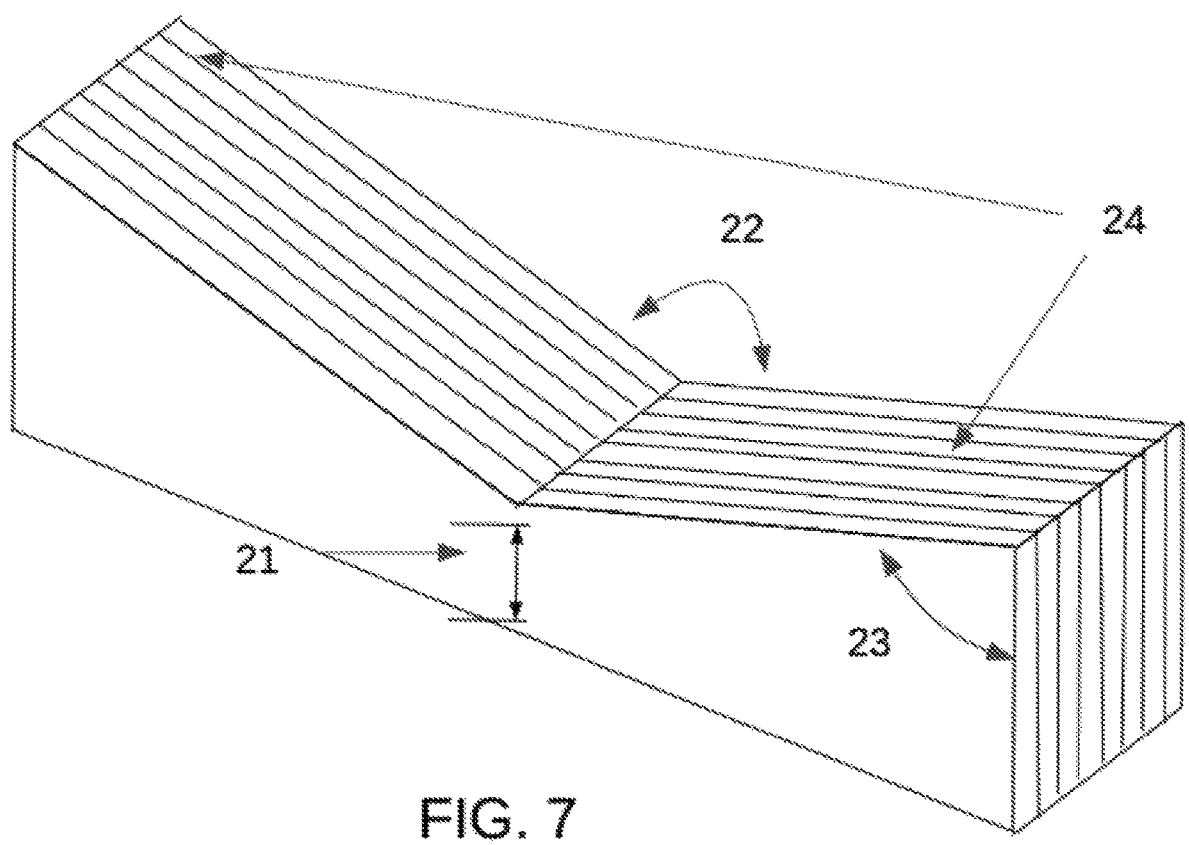
FIG. 7 is a depth expanded perspective view of an illustrative embodiment of the DEVICE depicting a taller variation composed of eight vertically laminated (i.e connected) layers, depicting the angles 23 and concave angulated dihedral 22 valley height 21.

FIG. 7 is a depth expanded perspective view of an illustrative embodiment of the DEVICE depicting a taller variation composed of eight vertically laminated (i.e connected) layers, depicting the angles 23 and concave angulated dihedral 22 valley height 21. 24 references two concave angulated user surfaces as examples. All surfaces are approximately flat. This embodiment may be used among other things for taller users or those with exceptional spinal range of motion, and not for the elderly who have very restricted and degenerated spines.

Figure 8:
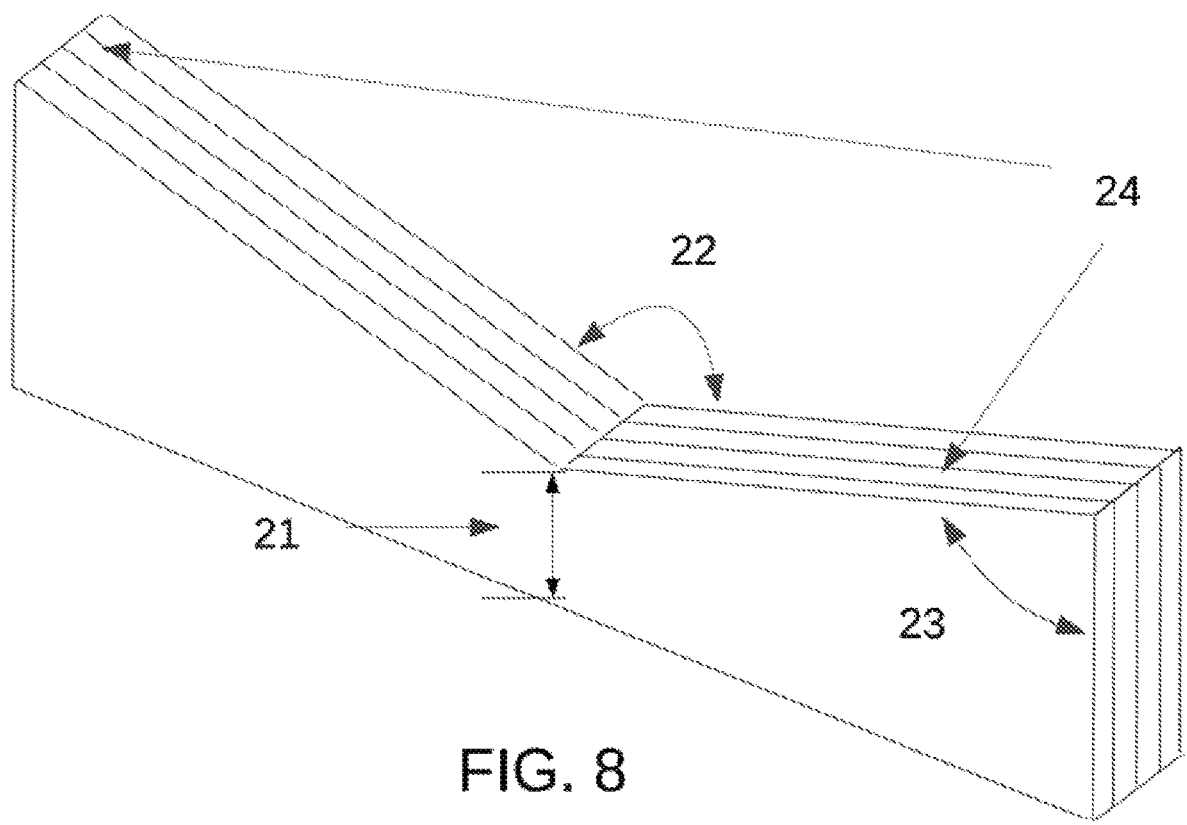
FIG. 8 is a depth expanded perspective view of an illustrative embodiment of the DEVICE depicting a narrower variation composed of four vertically laminated (i.e connected) subsections, depicting the angles 23 and concave angulated dihedral 22 valley height 21.

FIG. 8 is a depth expanded perspective view of an illustrative embodiment of the DEVICE depicting a narrower variation composed of four vertically laminated (i.e connected) subsections, depicting the angles 23 and concave angulated dihedral 22 valley height 21. 24 references two concave angulated user surfaces as examples. All surfaces are approximately flat. This embodiment may be used for users among other things with a tight neck and could use this supine while laying back on the DEVICE to conduct a workout.

Figure 9A:
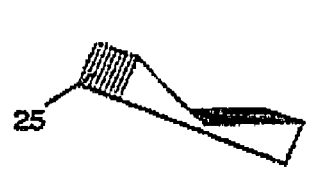
FIG. 9a is a front perspective view of an illustrative embodiment of the DEVICE that also demonstrates a vertical orientation of laminated layers surface 25 which is one of the at least two side surfaces that are substantially parallel to each other, where the other substantially parallel side surface is depicted in FIG. 9b as 27.
Figure 9B:
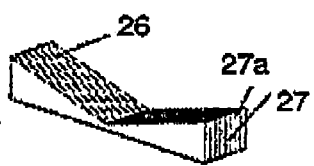
FIG. 9b is a rear perspective view of an illustrative embodiment of the DEVICE that further demonstrates a surface of a vertically oriented laminated layered surface 26 comprising a cradle for a body of a user, and vertical laminated sections 27a is viewed on the another surface 27 of the at least two side surfaces that are substantially parallel to each other.

FIG. 9 are perspective views of an illustrative embodiment of the DEVICE that also demonstrates a vertical orientation of laminated layers 25, 26, and 27 relative to the base and user contact composite surface. This embodiment additionally includes the various side surfaces, concave angulated surface or concave angulated dihedral user contact composite surface which forms a polyhedral presentation, a base surface, and the various edges, angles, and overall orientations as seen in other embodiments.

Figure 10A:
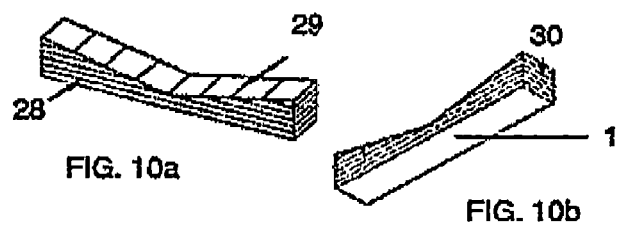
FIG. 10a is a front perspective view of an illustrative embodiment of the DEVICE that also demonstrates a horizontal orientation of laminated layers 28 relative to the user contact surface comprising a cradle for a body of a user, 29.
Figure 10B:
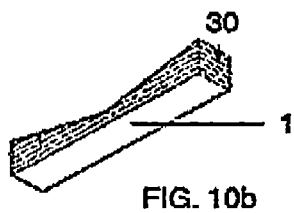
FIG. 10b is a base perspective view of an illustrative embodiment of the DEVICE that also demonstrates a horizontal orientation of laminated layers 30 relative to the base surface 1.

FIG. 10 are perspective views of an illustrative embodiment of the DEVICE that also demonstrates a horizontal orientation of laminated layers 28, 29, and 30 relative to the base surface and user contact composite surface. This embodiment additionally includes the various side surfaces, concave angulated surface or concave angulated dihedral user contact composite surface which forms a polyhedral presentation, a base surface, and the various edges, angles, and overall orientations as seen in other embodiments.

FIG. 11 are perspective views of an illustrative embodiment of the DEVICE that also demonstrates dihedral laminated layers 31 and 31*a*. This various orientation, among the other various orientations, could help offer a different user interaction based on the physical attributes of the user as well as the intended use, and/or method of use. These diagramed laminated layers 31, 31*a*, 32, 32*a*, and 33, which are also a variation of FIG. 10's horizontally orientated laminated layers 28, 29, and 30, are essentially parallel to the dihedral angulation 21*a* relative to the base surface 1 and user contact composite surface 2 and 3. The base surface 1 demonstrates 33 which is a proposed example of where the laminated layers may orientate along the base surface in this embodiment. Additionally, this embodiment also demonstrates a height variation of the substantially parallel side surfaces 32 and 32*a* which are analogous to side surfaces 4 and 5 from FIGS. 1-3, being substantially unequal to the height of 21 which is also listed in most of the other embodiments except 12, 12*a*, and 13. This embodiment additionally incorporates the various side surfaces, concave angulated surface or concave angulated dihedral user contact composite surface which forms a polyhedral presentation, a base surface, and the various edges, angles, and overall orientations as seen in other embodiments. Placing FIG. 11 before FIGS. 12, 12*a*, and 13 further assist the reader in visualizing their differences.

FIG. 12 is a perspective view of an illustrative embodiment of the DEVICE that also demonstrates a height variation of the substantially parallel side surfaces 34 and 35, which are analogous to side surfaces 4 and 5 from FIGS. 1-3, being substantially equal to the height of 21 which is also listed in FIG. 13 as well as FIGS. 5-8, 25, and 26. This embodiment demonstrates a blade-like presentation dihedral angulation relative to the base and user contact composite surface which additionally, but not limited to, helps demonstrate a proposed design for embodiments that are related to the device's capacity to be also used as a therapeutic tool as well as other similar uses at least described in this application. This proposed substantially equal height orientation could also afford the use of a material and density that allows for a use of the DEVICE while minimizing the DEVICE's overall size, perhaps to offer a pocket, hand held, or travel version DEVICE. Furthermore, 21*b* depicts an area within FIG. 12's concave angulation 21*a* that is referenced within this application as an incorporation of an apparatus for closure, folding, hinge, and/or other condensing mechanisms could be focused. This embodiment is a variation incorporating the addition of the closure area 21*b* as well as the substantially equal heights of 21, 34, and 35. FIG. 12 also additionally incorporates the remaining various side surfaces, concave angulated surface or concave angulated dihedral user contact composite surface which forms a polyhedral presentation, a base surface, and the various edges, angles, and overall orientations as seen in other embodiments.

FIG. 12*a* is a bottom view of an illustrative embodiment of the DEVICE that also demonstrates the base surface 1 consisting of surfaces 2*a* and 3*a*, the bottom view of the concave angulation 21*a*, as well as closure apparatus area 21*b*, and also the edges of the substantially parallel side surfaces 34 and 35, which are analogous to side surfaces 4 and 5 specifically seen in FIGS. 1-3, and FIG. 26. FIG. 12*a* also additionally incorporates the remaining various side surfaces, concave angulated surface or concave angulated dihedral user contact composite surface which forms a polyhedral presentation, a base surface, and the various edges, angles, and overall orientations as seen in other embodiments.

FIG. 13 is a perspective view of an illustrative embodiment of the DEVICE that also demonstrates a non closure variation of FIG. 12's substantially equal height variation of the substantially parallel side surfaces 34 and 35, which are analogous to side surfaces 4 and 5 from FIGS. 1-3, being substantially equal to the height of 21 which is also listed in FIG. 13 as well as FIGS. 5-8, 25, and 26. In this illustration height 21 is depicted without 21*b*'s closure embodiment from FIG. 12 or 12*a*. However, FIG. 13 does demonstrate the similarities of FIG. 12 overall presentation with dihedral concave contact surface's edge 21*a* and angle 22, as well as the angles 23 which represents the formation of the ridges of the at least one concave angulated surface seen in this as well as in all of the embodiments that are at least referenced in this application. Angulations 22 and 23 are also specifically depicted in at least FIGS. 5, 6, 7, 8, 25, and 26 as an example of these angles, as well as height 21 in all of the embodiments, even if not repetitively listed. FIG. 13 also additionally incorporates the remaining various side surfaces, concave angulated surface or concave angulated dihedral user contact composite surface which forms a polyhedral presentation, a base surface, and the various edges, angles, and overall orientations as seen in other embodiments.

Figure 14A:
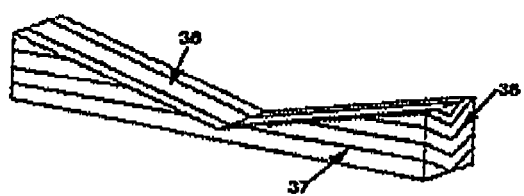
FIG. 14a is a front perspective view of an illustrative embodiment of the DEVICE that also demonstrates a dihedral laminated layers relative to surface 38 which is one of the at least two side surfaces that are substantially parallel to each other and 36 representing a surface of the at least one concave angulated surface comprising a cradle for a body of a user. 37 represents one of the at least two other side surfaces that are substantially parallel to each other.
Figure 14B:
FIG. 14b is a perspective view of an illustrative embodiment of the DEVICE that also demonstrates 39 the intersection of the dihedral laminated layers with base surface 1.

FIG. 14 are perspective views of an illustrative embodiment of the DEVICE that also demonstrates a different dihedral laminated layering this time seen from substantially parallel side surface 38 FIG. 14 is similar in other ways to FIG. 11 except for the orientation of laminated layers in 36, 37, and 38. This orientation could help offer a different user interaction based on the physical attributes of the user as well as the intended use, and/or method of use. Base surface 39 indicates a proposed orientation of the laminated layerings orientation from the bottom view and surface 36 from the top view. This embodiment additionally incorporates the remaining various side surfaces, concave angulated surface or concave angulated dihedral user contact composite surface which forms a polyhedral presentation, a base surface, and the various edges, angles, and overall orientations as seen in other embodiments.

Figure 15:
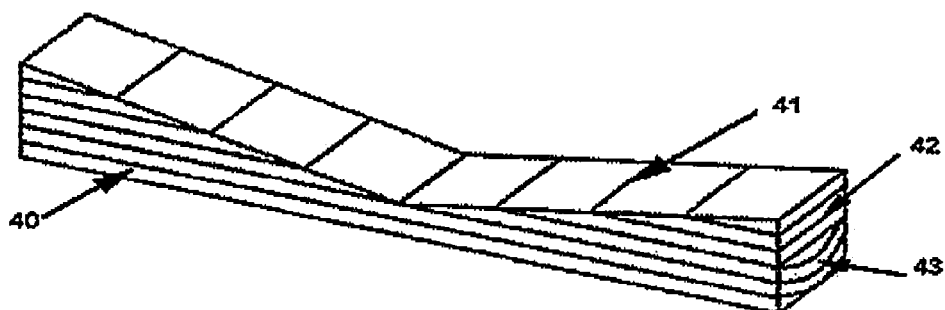
FIG. 15 is a perspective view of an illustrative embodiment of the DEVICE that also demonstrates a combination of horizontal and concave angulated laminated layers.

FIG. 15 is a perspective view of an illustrative embodiment of the DEVICE that also demonstrates a combination of an upper area 42 of horizontal laminated layers which is adjacent to the concave angulated user surface 41 and orientated above a lower or base surface layer 43 of concave rounded laminated layers 43. Number 40 represents either the front or rear view's proposed laminated layers orientation, as is also seen in other embodiments if not possibly specifically diagramed. This embodiment additionally includes the various side surfaces, concave angulated surface or concave angulated dihedral user contact composite surface which forms a polyhedral presentation, a base surface, and the various edges, angles, and overall orientations as seen in other embodiments.

Figure 16:
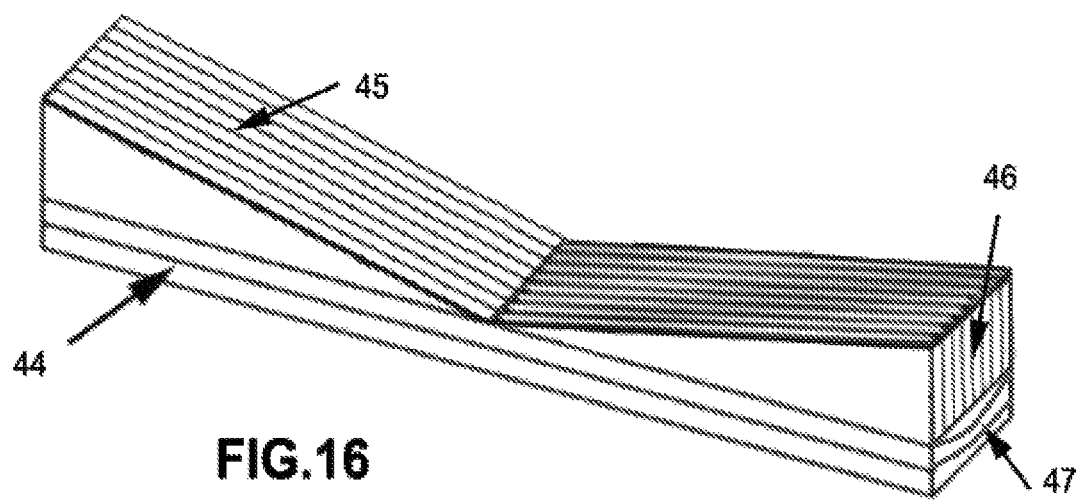
FIG. 16 is a perspective view of an illustrative embodiment of the DEVICE that also demonstrates a combination of vertical laminated layers and concave rounded laminated layer.

FIG. 16 is a perspective view of an illustrative embodiment of the DEVICE that also demonstrates a combination of an upper area 46 of vertical laminated layers which is adjacent to the concave angulated user surface 45 and orientated above a lower or base surface layer 47 of concave rounded laminated layers 47. Number 44 represents either the front or rear view's proposed laminated layers orientation, as is also seen in other embodiments if not possibly specifically diagramed. This embodiment additionally includes the various side surfaces, concave angulated surface or concave angulated dihedral user contact composite surface which forms a polyhedral presentation, a base surface, and the various edges, angles, and overall orientations as seen in other embodiments.

Figure 17:
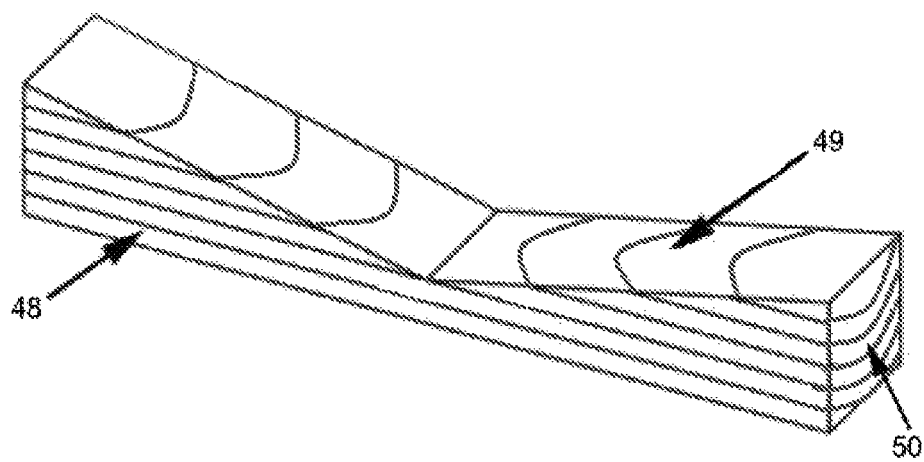
FIG. 17 is a perspective view of an illustrative embodiment of the DEVICE that also demonstrates an embodiment of concave rounded laminated layers 50 which are repeated.

FIG. 17 is a perspective view of an illustrative embodiment of the DEVICE that also demonstrates an embodiment of concave rounded laminated layers 50 which are repeated from the upper concave angulated user surface 49 downward and toward the lower or base surface layer. Number 48 represents either the front or rear view's proposed laminated layers orientation, as is also seen in other embodiments if not possibly specifically diagramed. This embodiment additionally includes the various side surfaces, concave angulated surface or concave angulated dihedral user contact composite surface which forms a polyhedral presentation, a base surface, and the various edges, angles, and overall orientations as seen in other embodiments.

Figure 18:
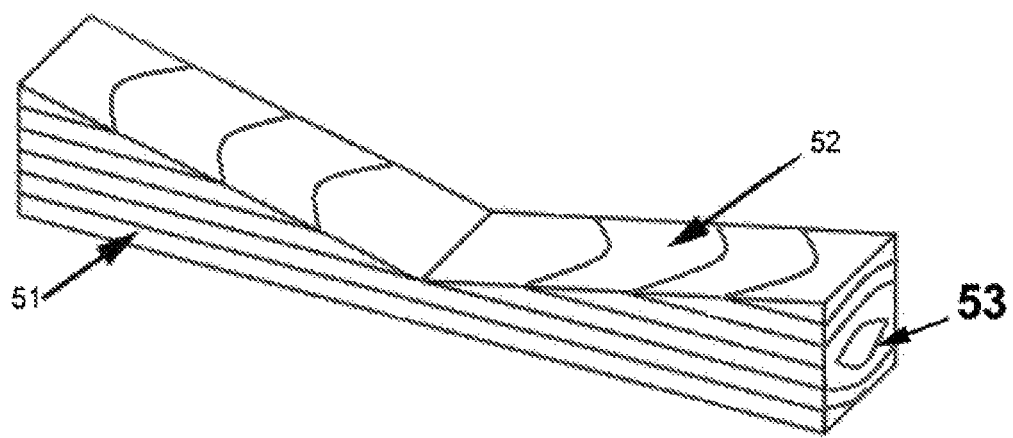
FIG. 18 is a perspective view of an illustrative embodiment of the DEVICE that also demonstrates an embodiment of cylindrical or elliptical laminated layers 53 which are repeated.

FIG. 18 is a perspective view of an illustrative embodiment of the DEVICE that also demonstrates an embodiment of cylindrical or elliptical laminated layers 53 which are repeated from the upper concave angulated user surface 52 downward and toward the lower or base surface layer. Number 51 represents either the front or rear view's proposed laminated layers orientation, as is also seen in other embodiments if not possibly specifically diagramed. This embodiment additionally includes the various side surfaces, concave angulated surface or concave angulated dihedral user contact composite surface which forms a polyhedral presentation, a base surface, and the various edges, angles, and overall orientations as seen in other embodiments.

Figure 19:
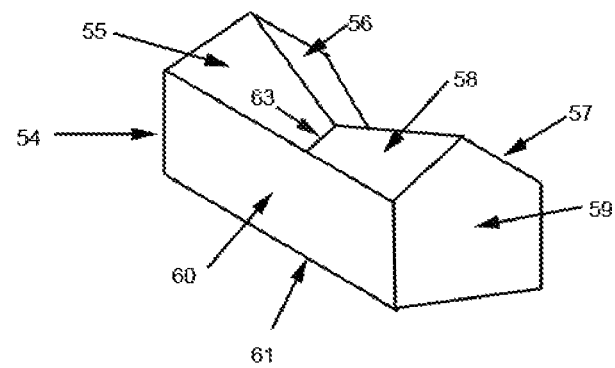
FIG. 19 is a frontal perspective view of an illustrative embodiment of the DEVICE that also demonstrates an embodiment of more than two concave angulated surfaces 55, 56, 57, and 58 forming concave edges.

FIG. 19 is a frontal perspective view of an illustrative embodiment of the DEVICE that also demonstrates an embodiment of more than two concave angulated surfaces 55, 56, 57, and 58 forming concave edges 63 and 64 (not seen here) forming concave vertex 65 (not depicted here) within the concave angulated surface or concave angulated dihedral user contact composite surface which forms a polyhedral presentation. The substantially parallel side surfaces 54 and 59 may be shaped as a pentagon to allow this embodiment's user contact composite surface shape to include ridges that run from the apex of each side surface's 54 and 59 pentagons to the concave vertex 65. The front side surface 60, or rear surface 62, also establishes the height 21 specifically diagrammed in other embodiments from essentially the lowest portion of this embodiment's concave angulated surface to the base 61. Concave surface connections angulations forming edges 63, 64, and concave vertex 65 form angle 22 depicted in other embodiments, for instance FIGS. 25 and 26. This embodiment, which includes various dimensions as do all other embodiments, referenced with FIG. 19, along with FIGS. 20 and 21, have further capacity to allow for greater positioning of a user's body for propping and/or supporting for, but not limited to, yoga positions, sex act positions, stretching, as well as any of the other uses or methods of use at least referred to in this application. This embodiment additionally includes the various side surfaces, concave angulated surface or concave angulated dihedral user contact composite surface which forms a polyhedral presentation, a base surface, and the various edges, angles, and overall orientations as seen in other embodiments.

Figure 20:
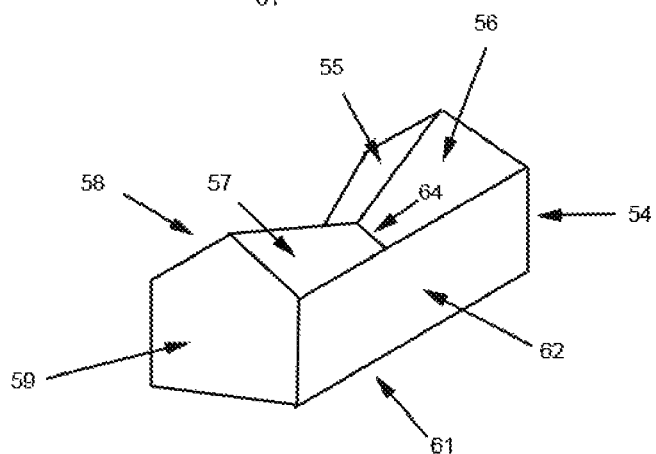
FIG. 20 is a rear perspective view of an illustrative embodiment of the DEVICE relative to FIGS. 19 and 21 that provides another view for orientation purposes of more than two concave angulated surfaces 58, 57, 55, and 56 forming concave edges.

FIG. 20 is a rear perspective view of an illustrative embodiment of the DEVICE relative to FIG. 19 that provides another view for orientation purposes of more than two concave angulated surfaces 58, 57, 55, and 56 forming concave edges 64 and 63 (not seen here) forming concave vertex 65 (not depicted here) within the concave angulated surface or concave angulated dihedral user contact composite surface which forms a polyhedral presentation. The rear view allows the arbitrary assigning of rear surface to 62, which is substantially identical to front surface 60. This relationship is indicated in other embodiments, such as FIGS. 2 and 3 with front surface 7 and rear surface 8, without the possible redundant labeling. This rear perspective view also depicts substantially parallel side surfaces 59 and 54 to be visualized from each side which is not specifically depicted in other embodiments because of their mirror-like relationship. This view shares the other statements in FIGS. 19 and 21.

Figure 21:
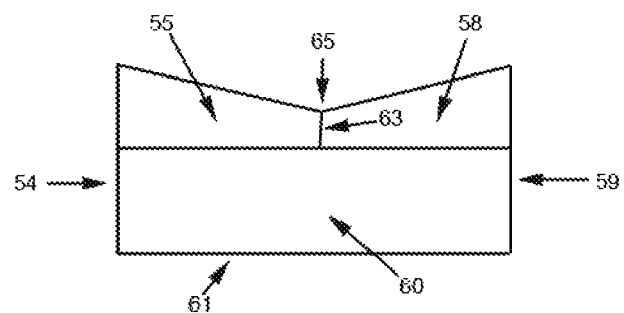
FIG. 21 is a front view of an illustrative embodiment of the DEVICE relative to FIGS. 19 and 20 that provides another view for orientation purposes of more than two concave angulated surfaces 55, and 58 and 56 and 57 (not seen surfaces) forming concave edges.

FIG. 21 is a front view of an illustrative embodiment of the DEVICE relative to FIGS. 19 and 20 that provides another view for orientation purposes of more than two concave angulated surfaces 55, and 58 and 56 and 57 (not seen surfaces) forming concave edges 63 and 64 (not seen here) forming concave vertex 65 within the concave angulated surface or concave angulated dihedral user contact composite surface which forms a polyhedral presentation. The front view allows the arbitrary assigning of frontal surface to 60, which is substantially identical to rear surface

62. This relationship is indicated in other embodiments, such as FIGS. 2 and 3 with front surface 7 and rear surface 8, without the possible redundant labeling. This front perspective view also depicts substantially parallel side surfaces 54 and 59 to be visualized from each side which is not specifically depicted in other embodiments because of their mirror-like relationship. This view shares the other statements in FIGS. 19 and 20 to help provide a 360 degree visualization of the various embodiments of the DEVICE.

Figure 22:
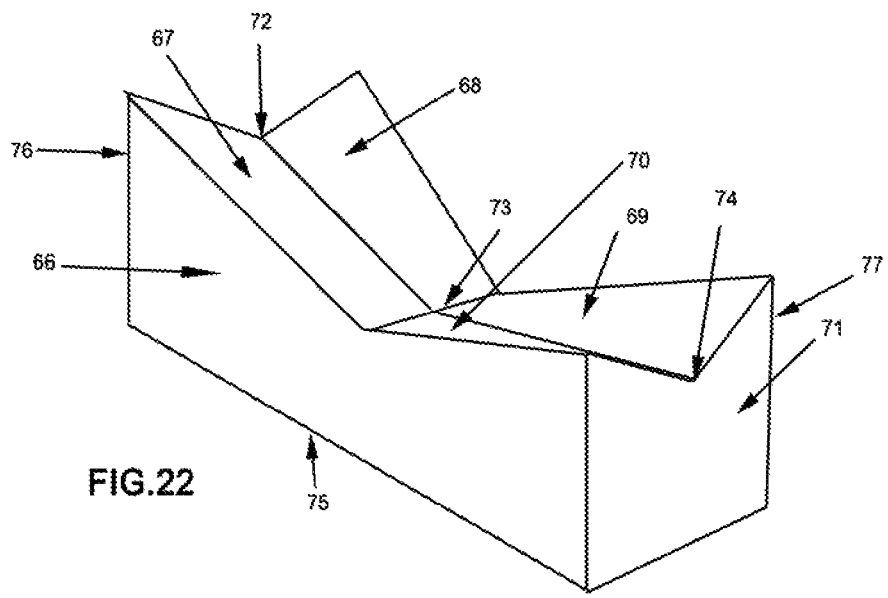
FIG. 22 is a perspective view of an illustrative embodiment of the DEVICE that, like FIGS. 19, 20, and 21, also demonstrates an embodiment of more than two concave angulated surfaces 67, 68, 69, and 70 forming concave edges.

FIG. 22 is a perspective view of an illustrative embodiment of the DEVICE that, like FIGS. 19, 20, and 21, also demonstrates an embodiment of more than two concave angulated surfaces 67, 68, 69, and 70 forming concave edges from vertex 72 to vertex 73 and from vertex 74 to vertex 73 forming an concave angulated channel with its most inferior point also referred to as 73. 73 may be manufactured as dihedral edge and/or as a level edge from front surface 66 to rear surface 77 within the concave angulated surface or concave angulated dihedral user contact composite surface which forms a polyhedral presentation. The substantially parallel side surfaces 71 and 76 with concave angulated vertices 72 and 74 may be shaped as a polygon to allow this embodiment's user contact composite surface shape to include side surface as well as front and rear side surfaces to contain the ridges that run to the concave vertex 73 in a channeled manner. The front side surface 66, or rear mirrored surface 77, also essentially establishes the concave angulation's height 21 specifically diagrammed in other embodiments from essentially the lowest portion of this embodiment's concave angulated surface to the base 75. This embodiment, which includes various dimensions as do all other embodiments, may provide further capacity to allow for greater positioning of a user's body for rubbing, stretching, distracting, massaging, kneading the user's extremities, especially the shoulder, as well as any of the other uses or methods of use at least referred to in this application. This embodiment additionally includes the various side surfaces, concave angulated surface or concave angulated dihedral user contact composite surface which forms a polyhedral presentation, a base surface, and the various edges, angles, and overall orientations as seen in other embodiments.

Figure 23:
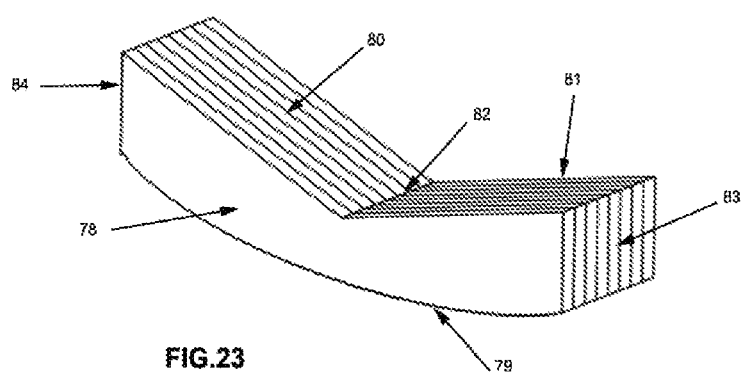
FIG. 23 is a perspective view of an illustrative embodiment of the DEVICE that also demonstrates a vertical orientation of laminated layers seen on surface 83 relative to the base surface 79, which is rounded in a rocking chair's rail configuration.

FIG. 23 is a perspective view of an illustrative embodiment of the DEVICE that also demonstrates a vertical orientation of laminated layers seen on surface 83 relative to the base surface 79, which is rounded in a rocking chair's rail configuration, and the upper user contact composite surface 80 and concave angulation edge 82. Front surface 78 and mirror rear surface 81 are adjoined by substantially parallel side surfaces 83 and 84's edge. This embodiment could be useful for a softer and more finely tuned interaction with the user especially for the massaging type of uses as well as balancing type uses. This embodiment additionally includes the various side surfaces, concave angulated surface or concave angulated dihedral user contact composite surface which forms a polyhedral presentation, a base surface, and the various edges, angles, and overall orientations as seen in other embodiments.

Figure 24:
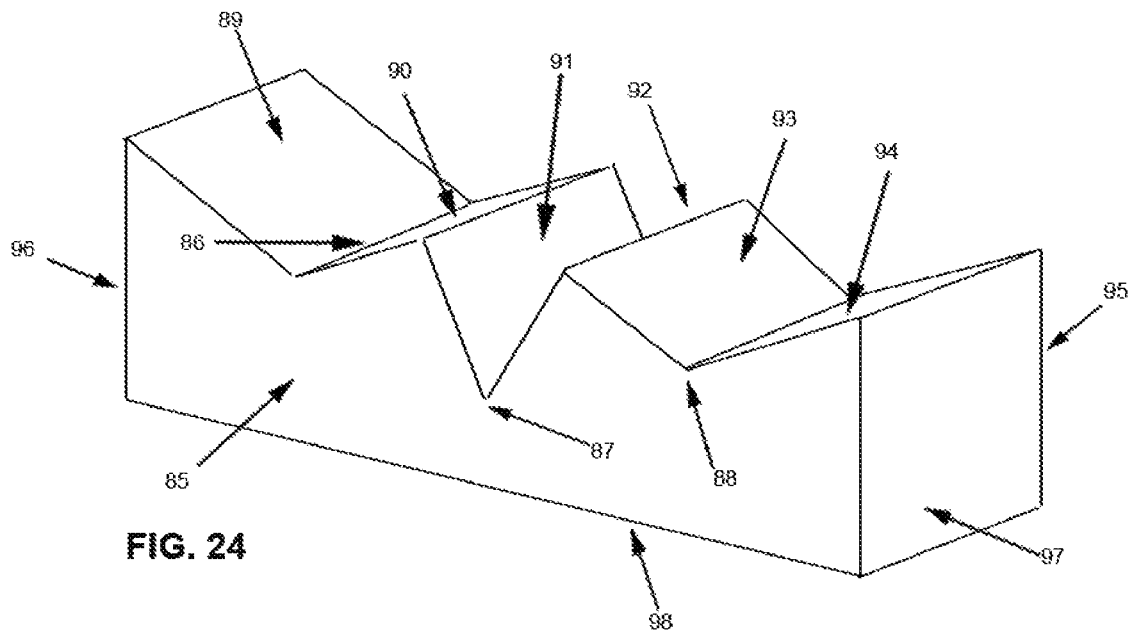
FIGS. 24 and 25 are respectively a perspective view and a frontal view of an illustrative embodiment of the DEVICE that also demonstrates an embodiment of more than two concave angulated surfaces 89, 90, 91, 92.
Figure 25:
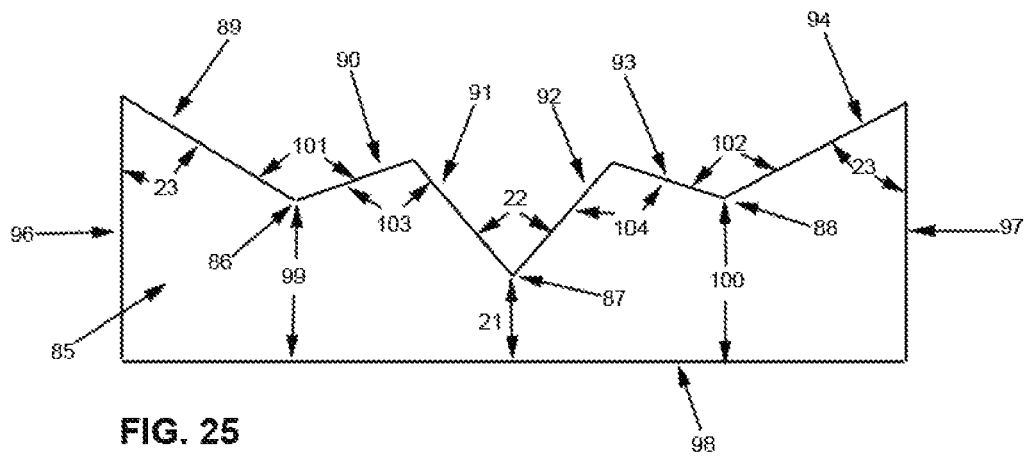

FIGS. 24 and 25 are respectively a perspective view and a frontal view of an illustrative embodiment of the DEVICE that also demonstrates an embodiment of more than two concave angulated surfaces 89, 90, 91, 92 (not seen here), 93, and 94 forming concave edges 86, 87, and 88 forming concave edges 86, 87 (not seen here), and 88 within the concave angulated surface or concave angulated dihedral user contact composite surface which forms a polyhedral presentation. The substantially parallel side surfaces 97 and 96 (seen here as its forward edge) may be shaped as a rectangular or square orientation to allow this embodiment's user contact composite surface shape perform a use of the DEVICE with multiple angulations and in this figure four ridges along the concave angulated surface that are formed by the angles 23, 23, 103, and 104. The angles 23, 103, and 104 reference the 1 to 89 degree mention as well as 22, 101, and 102 reference the 2 to 178 mention below:

At least 1 degrees elevation and not more than 89 degrees elevation as measured from a horizontal line that intersects with the edge of a concave angulation to the mean average tangent of any one centimeter run of a concave angulation; and where the opposing surface of a concave angulation is at least 1 degrees elevation and not more than 89 degrees elevation as measured from a horizontal line that intersects with the edge of a concave angulation to the mean average tangent of any one centimeter run of a concave angulation, where the angle of a concave angulation itself is at least 2 degrees and not more than 178 degrees as measured in a like manner also essentially forming a dihedral angle at the minimum point of the overall at least one concave angulated surface.

Furthermore, FIGS. 24 and 25 demonstrate that these referenced ranges are indicative of the angles required to complete the concave angulated surface or concave angulated dihedral user contact composite surface, as well as their corresponding ridges and edges, which forms a polyhedral presentation to some extent in all of the embodiments. The front surface 85 is substantially parallel to the mirror rear surface 95 (seen here as the lateral edge formed with the side surface 97). The base surface is 98, which is the same as base surface 1 in FIG. 1, as well as in other FIGS. the height 21 is depicted here to show the lowest or minimum point of the concave angulated surface as heights 99 and 100 originate from concave angulation edges 86 and 88 which are not the minimum point of the overall concave angulated surface. These FIGS. 24 and 25 along with FIG. 26 help better describe in greater detail the embodiment's variations within the stated abstract and claims range in this application. This embodiment, which includes various dimensions as do all other embodiments, referenced with FIGS. 24 and 25 have further capacity to allow for greater positioning of a user's body for more contact with the user in specific areas especially along the paraspinal regions of the spine, the extremities especially rubbing, kneading, massaging of the IT Band, the posterior rotator cuff, the posterior and lateral cervical spine, the anterior shin(s), the elbow(s), the wrist(s) as well as other uses of the DEVICE. This embodiment additionally includes the various side surfaces, concave angulated surface or concave angulated dihedral user contact composite surface which forms a polyhedral presentation, a base surface, and the various edges, angles, and overall orientations as seen in other embodiments.

Figure 26:
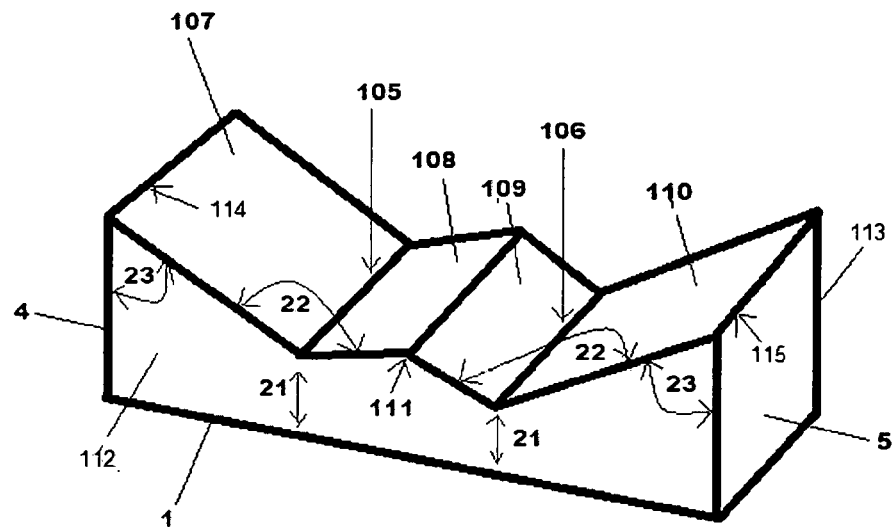
FIG. 26 is a perspective view of an illustrative embodiment of the DEVICE that also demonstrates an embodiment of more than two concave angulated surfaces 107, 108, 109, and 110 forming concave edges 105 and 106 and forming the ridge 111 from the connection of concave angulated surfaces 108 and 109.

FIG. 26 is a perspective view of an illustrative embodiment of the DEVICE that also demonstrates an embodiment of more than two concave angulated surfaces 107, 108, 109, and 110 forming concave edges 105 and 106 and forming the ridge 111 from the connection of concave angulated surfaces 108 and 109. This ridge is similar to the ridges or peaks formed at the tallest heights 114 and 115 of the substantially parallel side surfaces, 4 and 5 respectively, connections with a lateral and tallest aspect of a concave angulated surface, 107 and 110 respectively; all within the concave angulated surface or concave angulated dihedral user contact composite surface which forms a polyhedral presentation. The substantially parallel side surfaces that form the front 112 and rear 113 (seen here as its lateral edge with side surface 5's edge) surfaces may be shaped as a rectangular or square orientation to allow this embodiment's user contact composite surface shape perform a use of the DEVICE with multiple angulations and in this FIG. 26 along the concave angulated surface that are formed by the angles 23, 23, 22, and 22. This embodiment may further potentiate the effectiveness of the concave angulated surface for the various uses, including but not limited to, rubbing, massaging, kneading, oscillating, as well as propping and/or supporting the user's body for, but not limited to, yoga positions, sex act positions especially those involving a prone female to gain the interactive benefit of ridge 111, stretching, as well as any of the other uses or methods of use at least referred to in this application. This embodiment additionally includes the various side surfaces, concave angulated surface or concave angulated dihedral user contact composite surface which forms a polyhedral presentation, a base surface, and the various edges, angles, and overall orientations as seen in other embodiments.

FIG. 27 is a side view of an illustrative embodiment of the DEVICE utilized in a type of core and spine workout in which a user lies on the DEVICE 112 placed against and under the user in this drawing, although it can be used leaning back against a wall or other surface, the lower back and core 113 region, and above the pelvifemoral region 114, to allow for a use of the DEVICE, in a manner to provide contact with the concave angulated surface or concave angulated dihedral user contact composite surface which forms a polyhedral presentation. A use may include active spinal decompression movements possibly while the user is conducting active core exercises to help strengthen the area as well as to help initiate their body's own spinal disc pumping mechanism proposed elsewhere in this application. FIG. 27 further depicts the user choosing to better isolate one side of the core more than the other by pulling the left knee 117 to the chest past vertical and reaching towards the left knee with the left elbow 118 while the right knee 115 is well bent and the right foot 116 is placed gently on the floor. The unique active method of use is that the DEVICE can support the user's lower back and pelvis in a more anatomically friendly way, explained in this application, while performing the core exercises which can create an interaction with the user's spine in a proposed spinal decompressive action, both flexion and extension, are possible to occur while the user is also uniquely working out their core and related tissues.

FIG. 28 is a side view of an illustrative embodiment of the DEVICE utilized in a type of core, hip, thigh, and buttocks workout which also can stretch the lower spine 119, pelvis and hips 120 (lumbopelvifemoral region 119-120) when a user lies on the DEVICE 123 placed against and under the lower back and core 113 region, and above the pelvifemoral region 114, to allow for a use of the DEVICE, in a manner to provide contact with the concave angulated surface or concave angulated dihedral user contact composite surface which forms a polyhedral presentation. A use may include active spinal decompression movements especially in this embodiment of use the lumbosacral spine and lumbopelvifemoral region which includes the femur and thus thigh and lower extremity 121. This is shown in the diagram as well as a distinct knee to chest stretch 122 while the lumbosacral spine 119 is helped to be held into lumbosacral flexion thus allowing flexion spinal decompression of the lower discs in the spine. This can be maintained as a passive stretch and decompression as long as one knee is passively held to the chest. The concave angulated user surface allows for comfortable interaction with the posterior pelvis which makes for a comfortable stretch and/or concurrent active lower extremity 121 workout. The hip joint is freely decompressed as well which is beneficial for users with hip tightness and pain issues. The unique active method of use is that the DEVICE can support the user's lower back and pelvis in a more anatomically friendly way, explained furthermore in this application, to more safely and efficiently help the user.

FIG. 29 is a side view of an illustrative embodiment of the DEVICE utilized, among other things, in a type of inner thigh, hip, buttocks, and core workout which also can stretch or strengthen the lower spine 127, pelvis and hips 126 (lumbopelvifemoral region 127, 126, and 125) when a user lies on the DEVICE 124 placed against and under the pelvifemoral region 126 as well as further down the thigh under the IT Band 125 or beyond.

In FIG. 29, the DEVICE 124 is positioned to allow for a use of the DEVICE in a manner to provide contact with the concave angulated surface or concave angulated dihedral user contact composite surface which forms a polyhedral presentation. A use may include active hip exercises and/or more importantly in this embodiment of utilization the user may use the DEVICE as a rubbing, kneading, massaging, scratching, positioning, supporting, stretching, rehabilitating, and exercising tool. The user may slide the DEVICE further down the leg to under the ankle and roll on to their back supine and allow the knee to be stretched into extension. Restoring restricted knee extension is often the primary range of motion challenge a user is faced with during rehabilitation as well as fighting the aging process in the knee as well as the rest of the extremity joints of the body. Utilizing the DEVICE in an active oscillating interaction with the user is especially depicted in this embodiment. This oscillating motion is well described elsewhere in this application and visually referenced in FIG. 29.

At least one embodiment of the DEVICE comprises, but is not limited to, being manufactured with at least one step of additive manufacturing, subtractive manufacturing, lathing, turning, injection moulding, extrusion, blow moulding, casting, compression moulding, rotational moulding, transfer moulding, 3d printing, vacuum forming, welding, die casting, thermoforming, machining, vacuum casting, laminating, pouring, spraying, gluing, cutting, sawing, fastening, or pressure forming.

Additionally, in at least one embodiment, but not limited to, wherein the DEVICE comprising of at least one concave angulated surface comprises at least one of, but not limited to:

1. At least 1 degrees elevation and not more than 89 degrees elevation as measured from a horizontal line that intersects with the edge of a concave angulation to the mean average tangent of any one centimeter run of a concave angulation; and where the opposing surface of a concave angulation is at least 1 degrees elevation and not more than 89 degrees elevation as measured from a horizontal line that intersects with the edge of a concave angulation to the mean average tangent of any one centimeter run of a concave angulation, where the angle of a concave angulation itself is at least 2 degrees and not more than 178 degrees as measured in a like manner also essentially forming a dihedral angle at the minimum point of the overall at least one concave angulated surface.
2. The height from a concave angulated dihedral edge when measured through the shortest distance to the base surface being substantially equal to the heights of the at least two side surfaces that are substantially parallel to each other and are also substantially parallel to a plane that extends through the shortest distance from a concave angulated dihedral edge to the base surface being sufficient to support a use of the device.

3. The height from a concave angulated dihedral edge when measured through the shortest distance to the base surface being substantially unequal to the heights of the at least two side surfaces that are substantially parallel to each other and are also substantially parallel to a plane that extends through the shortest distance from a concave angulated dihedral edge to the base surface being sufficient to support a use of the device.

4. The distance between the at least two side surfaces that are substantially parallel to each other as well as being essentially parallel to a plane that extends through the shortest distance from a concave angulated edge to the base surface being sufficient to support a use of the device.

5. Or the distance between the at least two side surfaces that are substantially parallel to each other as well as being essentially perpendicular to a plane that extends through the shortest distance from a concave angulated edge to the base surface being sufficient to support a use of the device.

In several embodiments of the DEVICE, including but not limited to, FIG. 12, FIG. 12a, and FIG. 13, the interaction surface, which is a concave angulated surface, is described by the DEVICE having a concave angulated dihedral valley height number 21 substantially equal to the heights of each side surface 34 and 35 creating a concave angulated blade design. This embodiment's representation of the DEVICE may better produce a therapeutic tool as a handheld device for more specific use by a user including a healthcare practitioner, clinician, coach, trainer, and/or personal use. The ability to manufacture and subsequent dimensions of such a concave angulated blade design is based on the various materials, densities, apparatus, connections, and/or orientations that are offered in this document. This embodiment's height and overall dimensions may also be reduced as compared to other embodiments to, but not limited to, a thin metal, carbon, and/or a supportive enough material as based on the material's physical capacities to perform a use of the DEVICE. One primary function and method of use of this embodiment could be, but not limited to, as a therapeutic DEVICE that is operated by an apparatus, a clinician, a healthcare provider, and/or a person upon the body of the user receiving the application of the DEVICE.

Furthermore, a concave angulated embodiment may also, among other things, comprises an integration with at least one of, but not limited to: a supporting apparatus; a body affixing apparatus; a multi-tool apparatus; a therapeutic tool apparatus; an apparatus for sensing input; an apparatus for receiving input; an apparatus for producing output of data; or an incorporation with at least one of a closure apparatus at 21a and 21b where at least two surfaces of the device join to form, but not limited to, at least one concave angulated edge that incorporates, among other things, at least one of a hinge mechanism, a slide mechanism, a folding mechanism, a sliding mechanism, a compressing mechanism, a telescoping mechanism, a motorized hinge mechanism, a motorized positioning mechanism, a self-balancing hinge mechanism, a hydraulic hinge mechanism, a gimbaled balancing mechanism, a gimbaled positioning mechanism, or a closure mechanism, which also enables the device to, among other things, be condensed, be expanded, alter the device's orientation, alter the device's composition, alter at least one of the device's dimensions, alter the device's structure, or alter at least one angulated concave surface angle to accomplish additional use of the device.

Furthermore, another embodiment of the DEVICE includes that at least one surface is, but not limited to: ribbed, textured, undulating, knobbed, ridged, protruded, indented, retractable, telescoping, sound producing, not flat, light emitting, laser emitting, ultrasound emitting, ultraviolet light emitting, vibrating, infrared emitting, heating, percussing, electromagnetic spectrum emitting, electromagnetic field emitting, light-emitting diode emitting, ozone emitting, ion emitting, or microwave emitting.

In another embodiment of method of use the DEVICE may possibly be placed under and/or against a body part such as the ankle while supine, the knee is possibly stretched and/or exercised into extension. When the DEVICE is placed under and/or against the elbow when, among other things, supine in at least an anatomical position the elbow is possibly stretched and/or exercised into extension. When the DEVICE is placed under and/or against the cervical spine when supine, the cervical spine is placed, among other things, stretched, supported, and/or exercised into extension. Also, when the user is supine when the DEVICE is, among other things, placed under the ankle, the foot, the foot and ankle, and/or the toes can be stretched and/or exercised into plantar flexion passively, with effort, and/or with a weight on the dorsal surface of the foot. When the DEVICE is placed under and/or against the shin area when the user is, among other things, kneeling or prone the ankle, lower extremity, and/or front of the leg can be stretched and/or exercised, into at least plantar flexion. When the DEVICE is placed under and/or against the waist of the user when, among other things, prone spinal distraction, stretching, exercised, self-massaging against the DEVICE, self-rubbing against the DEVICE, and/or flexion or extension of the lumbosacral spine may be accomplished. From any of these passive positions of stretching, active exercises may also be performed. For example, when placed under the cervical spine when supine, chin retractions with resultant head and neck flexion can be performed. The DEVICE enhances active spinal extension and flexion along with strengthening the muscles of neck flexion that also help maintain and promote a proper cervical lordosis, and/or effected tissue function. For another example, the DEVICE possibly benefits lumbar, core, and/or lumbopelvic spine exercises in a similar fashion, especially the core muscles, specifically the psoas and iliopsoas muscles, are used to actively flex and extend the thoracolumbopelvic spine and/or pelvic-hip region. For example, when the supine user places the DEVICE under the spine and actively flexes the lumbopelvifemoral region the DEVICE may act as, at least but not limited to, a fulcrum like device and create a spinal action one of distraction, decompression, flexion, and/or extension due to, at least but not limited to, active core involvement.

Furthermore, another function of the DEVICE is, but not limited to, a use when attached and/or connected with an apparatus in at least this embodiment to a military field pack, back, a shoulder carrying device, and/or an otherwise backpack. This use is at least for a back support, portable back support, fixed back support, for dispersing a load, and/or improved comfort of the field pack's load against the soldier or wearer; and additionally, for a possible dual function as the DEVICE may be removed, because the DEVICE is at least one of, but not limited to, detachable or interchangeable via a connector, from its position, connection with the field pack and/or apparatus to furthermore be used by the soldier and/or backpack wearer for the DEVICE'S other uses of, but not limited to, stretching, exercising, positioning, rehabilitation, massaging, conditioning, and/or other uses described in this document. This applies to, but not limited to, while the soldier is on maneuvers or otherwise soldering on a mission or has returned to their base to help with self-care of their body pain, spinal loading, tissue use, tissue breakdown, dehydration, core strength, and/or fatigue incurred while using the field pack or backpack. These self-care areas may include at least the cervicothoracic-lumbopelvic regions, specific regions of the spine, pelvic-hip regions, upper extremities, lower extremities, and/or other body parts. This function could allow the soldier or user of the DEVICE fitted field pack or backpack to self treat or otherwise use the DEVICE themselves for neuromusculoskeletal pains and/or concerns typically experienced by soldiers and/or backpack user, especially, but not limited to their spine, neck, shoulders, extremities, muscles, thoracolumbopelvic, and/or pelvo-femoroacetabular regions. The DEVICE, could then be properly returned, or exchanged, to a connection with the field and/or general backpack device to be used for the back supportive capacities further described in this application.

In another embodiment the DEVICE incorporates the use of adding an enclosure wherein the enclosure is at least one of, but not limited to, a bag, a padded bag, a mesh, a strap, a sleeve, a cushion, a piece of fabric, a handle, a glove, a mitt, or a wrap. Also, the enclosure comprises of a material which is at least, but not limited to, one of foam, graphite, fiberglass, composite, gel, water, air, gas, fiber, plastic, microfiber, metal, sand, glass, ceramic, stone, metallic, polymer, resin, paper, cloth, wood, polycarbonate, silicone, rubber, wax, carbon fiber, Teflon, polyester, polymer, kevlar, dacron, water-resistant, waterproof, oil-resistant, oil proof, or organic material. The enclosure is helpful, but not limited to, by adding an additional layer of protection, improved hygiene, padding, cushioning, or a canvas for printing instructions of proper use, communication with the user's trainer, coach, or other healthcare provider, marketing, advertising.

The various figures denoted in this document refer to the various, but not limited to, designs of the device that are distinctly useful for creating different and/or separate results in the user. For instance the various densities and/or material combinations can result with different movements on and/or by the device and/or user like but not limited to wobbling, rocking, rolling, oscillating, rubbing, kneading, scratching, massaging, translating; and other motions that are referenced to in other parts of this document. These different motions and interactions with the user are possible because of the, including but no limited to, various layering designs that manufacturing can produce to form the substantially same and/or similarly shaped device comprising, but is not limited to, at least one volume of: a single essentially uniform volume which is possibly made of at least a single material; an integrated layering of at least one of, but not limited to, a vertical, a horizontal, an oblique, a random, a curved, or a combination of these various layering orientations which is possibly made of at least a single material; or at least two integrated layerings arranged in at least one of, but not limited to, a vertical, a horizontal, an oblique, a randomly, a curved, or a combination of these various layering orientations which is possibly made of at least a single material.

A method of using an angulated device for at least one of stretching, supporting, bracing, rehabilitating, positioning, massaging, kneading, scratching, or exercising a body of a user, the device comprising: at least one concave angulated surface, at least one base surface, at least two side surfaces that are substantially parallel to each other, and at least two other side surfaces that are substantially parallel to each other, comprising a stable DEVICE against which the user performs at least one activity of, but not limited to, stretching, supporting, bracing, rehabilitating, positioning, massaging, kneading, scratching, exercising, psoas muscle exercising, psoas muscle stretching, psoas muscle repairing, iliopsoas muscle exercising, iliopsoas muscle stretching, iliopsoas muscle repairing, shoulder exercises, shoulder stretches, rotator cuff exercises, rotator cuff stretches, elbow exercises, elbow stretches, wrist exercises, wrist stretches, hand exercises, hand stretches, finger exercises, finger stretches, hip exercises, hip stretches, knee exercises, knee stretches, ankle exercises, ankle stretches, foot exercises, foot stretches, plantar fascia exercises, plantar fascia stretches, toe exercises, toe stretches, pelvic tilting, core exercises, pelvic tilting from core muscular activity, chin retractions, spinal exercises, spinal stretches, spinal decompression, spinal traction, spinal range of motion improvement, extremity exercises, extremity stretches, extremity joint stretches, extremity joint distraction, extremity joint labral decompression, extremity joint exercises, extremity joint traction, extremity joint range of motion improvement, supporting, positioning, gliding, oscillating, rubbing, sliding, rolling, rocking, wobbling, sitting, reclining, lying, walking, running, hiking, backpacking, carrying a travel pack, wearing a fanny pack, carrying a child carrier, carrying a pet carrier, pet care device, an animal care device, a veterinary animal care device, carrying a mail carrier's pack, carrying a backpack, carrying a firefighter's pack, carrying a military field pack, carrying a military pack, carrying a rucksack, carrying a military weapon, wielding a military weapon, wielding a weapon, carrying a weapon, carrying furniture, carrying appliances, carrying equipment, carrying a scuba pack, scuba diving, riding a motorcycle, biking, bicycling, tricycling, piloting, driving, massaging, kneading body tissues, sleeping, meditating, performing yoga, performing a sex act, performing thi chi, resting, kite surfing, surfboarding, windsurfing, parasailing, parachuting, firefighting, balancing, strengthening, rowing, using an ergometer, using a harness to transfer a person, using a harness to transfer a patient, using a rowing machine, rowing a boat, rowing a scull, kayaking, pet neuromusculoskeletal care, animal neuromusculoskeletal care, veterinary neuromusculoskeletal animal care, animal self-rubbing device, animal self-rubbing device for the purpose of revealing a habit which is also used in a diagnostic sense for a care giver to further care for the animal, or exercising.

Furthermore, a method of use of the DEVICE may also include, but not limited to, the activity comprising of at least one of:

1) Active chin retraction with the dorsal cervical spine pressing against the positioned device (this is a similar motion to FIG. 27 except the DEVICE is placed under or against the back of the lower cervical spine and the neck is moved into the DEVICE) while the user is at least supine creates a unique concentric force via the related neuromusculoskeletal tissues leveraged against the at least one concave angulated surface of the device which action initially lifts the head from the initial at least supine supported cervical lordotic position into supported cervical flexion then the head is subsequently lowered by the user with alternating cycles from concentric chin retraction to eccentric chin retraction which then returns the flexed cervicothoracic spine to its original position.

2) Active chin retraction with the dorsal cervical spine pressing against the positioned device while the user is at least upright creates a unique concentric force via the related neuromusculoskeletal tissues leveraged against the at least one concave angulated surface of the device which action initially lifts the head from the initial at least upright supported cervical lordotic position into supported cervical flexion then the head is subsequently lowered by the user with alternating cycles from concentric chin retraction to eccentric chin retraction which then returns the flexed cervicothoracic spine to its original position.

3) Active pelvic tilting FIG. 27 with the at least upper lumbar spine 113 pressing against the positioned device 112 while the user is, at least one of but not limited to, supine, seated, or upright creates an unique concentric force by the related neuromusculoskeletal core tissues leveraged against the at least one concave angulated surface of the device which action initially concentrically lifts the lumbopelvic spine from supported lordosis into supported lumbopelvic flexion then the pelvis is subsequently eccentrically lowered by the user with alternating cycles from concentric lumbopelvic flexion to eccentric lumbopelvic flexion which then returns the lumbopelvic spine to its original position during the performance of this core musculoskeletal activity.

4) Pelvifemoral tilting motions FIG. 27 at least one of, but not limited to: passive knee(s) to chest stretches, active pelvic tilting, active hip(s) flexion, or active core exercises with the user at least one of supine, seated, side lying, prone, or upright while positioning the device at least under or behind the hips posterior to the pelvifemoral joint subsequently stretches and reduces the lumbopelvic spine's expected lordosis by the device's interaction with the neuromusculoskeletal tissues of the lumbopelvic spine via the lumbopelvic spine being leveraged against the device's concave angulated surface initiating at least one of, but not limited to, a decompressive or a flexion-distraction stretch.

5) Among other things hip stretches originating from a single knee to chest stretch position FIG. 28 with the user positioned, at least one of but not limited to, supine, seated, side lying, prone, or upright while positioning the device under the hips posterior to the pelvifemoral joint subsequently reduces the normal lumbopelvic spine's lordosis by the device interacting with the user's neuromusculoskeletal tissues of the lumbopelvic spine further toward a greater degree of lumbopelvic flexion via the lumbopelvic spine being leveraged against the device's concave angulated surface while additionally the other lower extremity is placed downward, not pulled to the chest, into an outstretched hip extension position resulting in that hip joint undergoing at least one of, but not limited to, an additional leveraged extension, possible distraction force, or another motion of stretching is performed relative to the device's more distinctly supported isolated neuromusculoskeletal pelvifemoral joint than if performing the same basic overall combined lumbopelvifemoral neuromusculoskeletal stretch without the device.

6) Among other things hip exercises originating from a single knee to chest stretch position FIG. 28 with the user positioned, at least one of but not limited to, supine, seated, side lying, prone, or upright while positioning the device under the hips posterior to the pelvifemoral joint subsequently reduces the normal lumbopelvic spine's lordosis by the device interacting with the user's neuromusculoskeletal tissues of the lumbopelvic spine further toward a greater degree of lumbopelvic flexion via the lumbopelvic spine being leveraged against the device's concave angulated surface while additionally the other lower extremity is placed downward, not pulled to the chest, into an outstretched hip extension position resulting in that hip joint undergoing at least one of, but not limited to, an additional leveraged extension, a possible distraction force, or another device supported motion while the exercise is performed relative to the device's more distinctly supported isolated neuromusculoskeletal pelvifemoral joint than if performing the same basic overall combined lumbopelvifemoral neuromusculoskeletal stretch without the device.

7) Among other things positioning an extremity joint (see FIG. 29 in brief descriptions section for further explanation) with the user positioned, at least one of but not limited to, supine, seated, side lying, prone, or upright while positioning the device against the area neighboring the extremity joint to allow for an activity at least one of, but not limited to, supporting, bracing, rehabilitating, positioning, oscillating, rolling, rubbing, kneading, scratching, massaging, exercising, stretching, sustained stretching, or applying a force into the extremity joint one of at least extension, flexion, or rotation.

8) Additionally, among other things the user positions a part of their body in any conceivable way FIG. 28, 29 against the at least one concave angulated surface of the device which interaction also possibly constitutes at least one of a fulcrum, a lever, or being capable of dispersing a load during the interaction between the device and a volume of the user's tissues which encourages a force that passes through the entire volume of the user's contacting tissues when the user actively moves their body part which possibly acts as a moving lever on the substantially continually connected device which possibly acts as a fulcrum for the tissue union in at least an oscillating direction which translates the mounting force along the entire volume of the tissues interacted with which are now also moving directionally with the substantially same oscillating distance as a thus resulting at least massaging motion is encouraged without the device specifically rolling off of the interaction with the volume of the user's body by the device's concave angulated surface which thus helps maintain a continued force throughout the oscillating distance and direction traveled by the active movement with the at least mostly entire volume of the body part compressed against the substantially maintained leveraged interaction with the device.

Further including that the activity comprising of at least one of passive or active movements by the device. Further including that the activity FIG. 29 comprising of at least one of: stimulating proprioceptors, stimulating non-pain-producing mechanoreceptors, stimulating nociceptors, or stimulating the vestibular system.

Wherein the activity includes stimulating at least one of, but not limited to: afferent impulses from the periphery to the central nervous system, neurological tissue, the release of endorphins, the descending inhibitory pathways, the subsequent depression and/or inhibition of contractile tissues, the subsequent depression and/or inhibition of pain promoting tissues, the subsequent sense of relaxation of the body, the subsequent sense of relaxation of the mind, the subsequent sense of relaxation of the spirit, or the subsequent sense of relaxation of the soul of the user. Further including that the activity comprising of at least one of passive or active movements by an apparatus that connects to the device.

Also including that the activity comprising of at least one of, but not limited to: stimulating proprioceptors, stimulating non-pain-producing mechanoreceptors, stimulating nociceptors, or stimulating the vestibular system. Wherein the activity includes stimulating at least one of, but not limited to: afferent impulses from the periphery to the central nervous system, neurological tissue, the release of endorphins, the descending inhibitory pathways, the subsequent depression and/or inhibition of contractile tissues, the subsequent depression and/or inhibition of pain promoting tissues, the subsequent sense of relaxation of the body, the subsequent sense of relaxation of the mind, the subsequent sense of relaxation of the spirit, or the subsequent sense of relaxation of the soul of the user.

Further including that the activity comprising of at least one of tissue repair, healing, physiologic equilibrium, a beneficial mental state, a beneficial emotional state, a state of relaxation, improved neuromusculoskeletal system, improved circulatory system, improved lymphatic system, a beneficial energetic state, proposed proper spinal disc pump imbibition action which is at least beneficial to allow for proper healing but not limited to at least one of after disc injury, overloading, immobility, decreased range of motion, mechanical damage, wear and tear, hypomobility, hypermobility, reduced disc failure properties, altered cell level signals, matrix remodeling, incomplete healing, reduced motion segment function, pain, or degenerative changes.

The process of manufacturing may include at least one of, but not limited to, at least one step of of additive manufacturing, subtractive manufacturing, lathing, turning, injection moulding, extrusion, blow moulding, casting, compression moulding, rotational moulding, transfer moulding, 3d printing, vacuum forming, welding, die casting, thermoforming, machining, vacuum casting, laminating, pouring, spraying, gluing, cutting, sawing, fastening, or pressure forming.

Also, the DEVICE may be held and/or supported by a person, body therapist, owner, veterinarian, and/or an apparatus when used, among other things, against an animal for the same and/or similar uses that are expressed in this document for users. The DEVICE may also be used with and/or by animals as a self-rubbing device by placing or mounting the DEVICE in at least, but not limited to, one of the DEVICE's embodiments against a secure surface and/or an apparatus to allow the animal to rub themselves against the DEVICE. For example, the DEVICE may be installed in a stall, on a fence, on a tree, on a building, and/or on a wall for an animal like, but not limited to, a dog, a cat, a cow, a goat, a donkey, a deer, a zoo animal, an elephant, or a horse for the animal to rub themselves against the DEVICE. This embodiment could be well received especially by horse owners for their horses when in a stall and/or horse trailer commonly rub against the stall walls and damage the walls creating a problem for the owner.

Also, when the DEVICE is possibly used in this manner the owner or caregiver may discover useful health information if the animal demonstrates a revealing habit with the self-rubbing against the DEVICE that could then be used in a diagnostic sense to further care for the animal.

The device my be used as a neuromusculoskeletal support for humans during sex acts for more comfort, flexibility, better positioning for physical stimulation relative to the nature of the act. The gabled design, FIGS. 19-21 and 26, embodiment is a good example, but not limited to this embodiment, to function as such a sex act support. Similar positioning of this device is also beneficial for, but not limited to, various exercises like yoga.

Furthermore, other embodiments may be sized to address the needs of the pediatric, adult, elderly, obese, domestic pet, athlete, large animal, hand held device, back pack, ruck sack, and other uses described in this application from, including but not limited to, ones that incorporate a FIG. 5 angle number 23 ranging from approximately 1 to 89 degrees, a FIG. 6 number 22 dihedral angle ranging from approximately 2 to 178 degrees, as well as a height of FIG. 5 of number 21 ranging from approximately 1/32" to 8", a FIG. 1 height of side surfaces numbered 4 and 5 ranging from approximately 2.5" to 18", a FIG. 2 top view width of surfaces 2, 3, and edges 6 from ranging from approximately 0.5" to 36", and a FIG. 1 length of base surface 1 ranging from approximately 4" to 36".

The embodiments described above are only to exemplify the present invention but not to limit the scope of the present invention. Therefore, any equivalent modification or variation according to the shapes, structures, features, or spirit disclosed by the present invention is to be also included within the scope of the present invention.

A number of embodiments have been described. Nevertheless, persons skilled in the art will understand the devices and methods specifically described herein and illustrated in the accompanying figures are non-limiting exemplary embodiments, and that the specification and figures should be construed merely exemplary of particular embodiments. It is to be understood, therefore, that the present disclosure is not limited to the precise embodiments described, and various other changes and modifications may be effected by persons skilled in the art without departing from the spirit and scope of the disclosure. It is also envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, those skilled in the art will envision other embodiments within the scope and spirit of the following claims.

The above description is intended to illustrate exemplary embodiments of the invention, which will be best understood in conjunction with the detailed description to follow, and are not intended to limit the scope of the invention. Additionally, heretofore Applicant's invention has been described using the transitional phrase "comprising." As will be readily apparent to one skilled in the art, Applicant's invention as described herein can also be defined with all of the same components as discussed above using the transitional phrase "consisting essentially of" in place of "comprising" to exclude any extra elements or components not described that materially affects the basic and novel characteristics of Applicant's invention.

The invention claimed is:

1. A concave angulated device for at least one of: stretching, supporting, bracing, rehabilitating, positioning, massaging, kneading, scratching, exercising, or neuroplasticity stimulation of a body of a user; the device comprising:
   at least one concave angulated surface, at least one base surface, at least two side surfaces that are substantially parallel to each other, and at least two other side surfaces that are substantially parallel to each other, further comprising the at least one concave angulated surface is characterized by a polyhedral presentation comprising at least two or more surfaces intersecting at one or more substantially dihedral angles comprising a cradle for a body of a user where the terminal ends of the at least one concave angulated surface are taller, relative to the base surface, than any other edge that is further comprised within the polyhedral presentation: furthermore, the mode of use of the concave angulated device is characterized by orienting the at least one concave angulated surface substantially perpendicular to and against the long axis of a portion of a user.

2. A device according to claim 1, further comprising the use of the device by a user comprises at least one of;
passive spinal intervertebral disc decompression, active spinal intervertebral disc decompression, passive spinal intervertebral disc flexion distraction, active spinal intervertebral disc flexion distraction, passive spinal intervertebral disc extension distraction, active spinal intervertebral disc extension distraction, the spinal disc pump, spinal intervertebral disc imbibition, spinal intervertebral disc repair, spinal intervertebral disc hydration, spinal intervertebral disc inflammation reduction, spinal intervertebral disc debris reduction, spinal joint anatomic effects, spinal joint physiologic effects, spinal traction, extremity joint anatomic effects, shoulder rehabilitation, extremity joint physiologic effects, joint decompression, joint hydration, joint repair, joint distraction, joint traction, muscle repair, muscle stretching, muscle elongation, muscle strengthening, muscle relaxation, muscle spasm relaxation, tendon repair, tendon stretching, tendon strengthening, ligament repair, ligament strengthening, ligament stretching, cartilage repair, cartilage hydration, disrupting scar tissue, disrupting the formation of scar tissue, elongating scar tissue, elongating neurological tissues, decreasing fluid accumulation, improving fluid drainage, improving circulation, improving lactate equilibrium, improving lymphatic flow, improving tissue drainage, improving tissue elasticity, tissue repairing, tissue healing, tissue rubbing, muscle rubbing, self-rubbing, physiologic equilibrium, promoting a beneficial mental state, promoting a beneficial emotional state, promoting a state of relaxation, promoting a healthy neuromusculoskeletal system, promoting a beneficial energetic state, promoting a beneficial stimulation to address traumatic brain trauma issues, promoting a beneficial stimulation to address post-traumatic stress issues, promoting a beneficial stimulation to address concussion issues, or promoting an improved spinal disc pump imbibition action; further comprises the use is at least beneficial for improved spinal motor unit or joint healing comprising at least one of:
after disc injury, disc overloading, abnormal immobility, abnormal decreased range of motion, mechanical damage, wear and tear, hypomobility, hypermobility, disc failure properties, altered cell level signals, matrix remodeling, incomplete healing, reduced motion segment function, pain, or degenerative changes; furthermore, stimulating at least one of:
neuroplasticity, neural plasticity, brain plasticity, neuroplastic changes in a body of a user, neuroplastic subluxation, proprioceptors, non-pain-producing mechanoreceptors, nociceptors, the vestibular system, afferent impulses from the periphery to the central nervous system, neurological tissue, the release of endorphins, descending inhibitory pathways, depression or inhibition of contractile tissues, depression or inhibition of pain promoting tissues comprising substance P release, the placebo effect, the Pavlovian response, or a sense of relaxation.

3. A device according to claim 1, further comprising the device is manufactured to comprise at least one type of material.

4. A device according to claim 3, further comprising the at least one type of material comprises at least one of:
foam, graphite, fiberglass, composite, gel, water, air, gas, liquid, fiber, plastic, microfiber, metal, sand, glass, ceramic, stone, metallic material, organic polymer, resin, paper, cloth, wood, polycarbonate, silicone, rubber, wax, carbon fiber, Teflon, polyester, kevlar, dacron, water-resistant material, waterproof material, oil-resistant material, oil proof material, electromagnetic material, electromagnetic absorbent material, electromagnetic modifying material, electromagnetic emitting material, electromagnetic dispersing material, magnetic material, light refracting material, light emitting material, light reflecting material, light magnifying material, light dispersing material, light condensing material, light compressing material, sound magnifying material, sound emitting material, sound dampening material, liquid absorbent material, liquid dispersing material, beat absorbent material, heat dispersing material heat emitting material, gas absorbent material, freezable material, fungal material, or organic material.

5. A device according to claim 4, further comprising the at least one type of material comprises at least one of an integrated layer, an integrated layering, a volume, or layers.

6. A device according to claim 4, further comprising the device comprises at least one compressible material.

7. A device according to claim 4, further comprising the device comprises at least one volume of a substantially uniform material which is manufactured of at least;
a single material; an integrated layering of at least one of a vertical, a horizontal, an oblique, a curved, or a combination of these various layering orientations, which is manufactured of at least a single material; or further comprising at least two integrated layerings arranged in at least one of a vertical, a horizontal, an oblique, a curved, or a combination of these various layering orientations which is manufactured of at least a single material.

8. A device according to claim 1, further comprising the device is manufactured to comprise at least one step of:
additive manufacturing, subtractive manufacturing, lathing, turning, injection moulding, extrusion, blow moulding, casting, compression moulding, rotational moulding, transfer moulding, three dimensional printing, vacuum forming, welding, die casting, thermoforming, machining, vacuum casting, laminating, pouring, spraying, gluing, freezing, cutting, sawing, fastening, trimming, sanding, stamping, pouring, vibrating, heating, cooling, slicing, mixing, or pressure forming.

9. A device according to claim 8, further comprising the device comprises an integration with at least one of:
an apparatus for creating or inducing motion within the device, an apparatus for creating or inducing motion of the device, e an apparatus supporting a body of a user a body of a user affixing apparatus, a multi-tool apparatus, a therapeutic tool apparatus, an electromagnetic apparatus, an electromagnetic managing apparatus, a magnetic apparatus, an apparatus for sensing or recording information, an apparatus for receiving information, an apparatus for producing or transmitting output of information, an apparatus comprising at least one speaker, an apparatus comprising at least one projector, an apparatus comprising at least one percussing device, an apparatus comprising at least one vibrating device, or an apparatus integrating a connection for at least two surfaces; further comprising a cradle that comprises at least one of:

a hinged mechanism, a slide mechanism, a folding mechanism, a sliding mechanism, a compressing mechanism, a telescoping mechanism, a motorized hinge mechanism, a motorized positioning mechanism, a self-balancing hinge mechanism, a balancing mechanism, a hydraulic hinge mechanism, a gimbaled balancing mechanism, a gimbaled positioning mechanism, or an adjustment mechanism which enables the device to be;

condensed, collapsed, consolidated, expanded, contracted, or altered in orientation relative to the device's dimensions or the at least one concave angulated surface.

10. A device according to claim 8, further comprising the device comprises at least an integration into one of a:

backpack, travel pack, bench press, stand alone bench press, fanny pack, child carrier, pet carrier, military field pack, rucksack, mail carrier's pack, firefighter's pack, astronaut's pack, astronaut's suit, military astronaut's suit, astronaut propulsion unit, jet suit, weapon carrying harness, furniture moving harness, appliance carrying harness, equipment carrying harness, scuba tank, scuba pack, back support section of all seats, chair, couch, sofa, recliner, bed, med bed, meditation bed, hospital bed, rocking chair, cockpit seat, automobile seat, automobile seat cushion, automotive racing seat construction equipment seat, off road vehicle seat, airplane seat, warcraft seat, military aircraft seat, military spacecraft seat, spacecraft seat, portable automobile seat cushion, portable seat cushion, motorcycle seat, snowmobile seat, parachute harness, spinal back support, lumbar back support, lumbar back brace, parachute pack, kitesurfing harness, windsurfing harness, boardsailing harness, parasailing harness, spacesuit, body armor, clothing, an exercise device, therapeutic device, therapeutic tool, tool bit, rotary tool bit, oscillating tool bit, reciprocating tool bit, examination table, treatment table, chiropractic treatment table, chiropractic examination table, physical therapy treatment table, physical therapy examination table, proprioceptive rehabilitation board, proprioceptive rehabilitation device, rehabilitation device, rehabilitation equipment, spinal decompression table, flexion extension table, flexion extension therapeutic table, flexion distraction device, flexion distraction table, flexion distraction chiropractic table, inversion table, inversion traction device, inversion stretching device, inversion decompression device, massage table, massaging chair, massaging table, recliner, couch, wall, weight bench, sex act support device, yoga support device, yoga mat, exercise mat, physio ball, physio ball chair, office chair, pilates support device, pilates device, pilates reformer, saddle, bicycle seat, tricycle seat, recumbent bicycle seat, stationary bicycle seat, spinning bike seat, rowing machine seat, rowboat seat, rowing scull seat, kayak seat, kayak back support, wheelchair, physically impaired person lift, harness for the physically Impaired, boat seat, pet care device, an animal care device, veterinary animal care device, self-rubbing device, animal self-rubbing device, mounted animal self-rubbing device, weight belt, or a device to promote at least one of:

tissue repairing, tissue healing, tissue rubbing, muscle rubbing, self-rubbing, physiologic equilibrium, promoting a beneficial mental state, promoting a beneficial emotional state, promoting a state of relaxation, promoting a healthy neuromusculoskeletal system, promoting a beneficial energetic state, promoting a beneficial stimulation to address traumatic brain trauma issues, promoting a beneficial stimulation to address post-traumatic stress issues, promoting a beneficial stimulation to address concussion issues, or promoting an improved spinal disc pump imbibition action; further comprises the use is at least beneficial for improved spinal motor unit or joint healing comprising at least one of;

after disc injury, disc overloading, abnormal immobility, abnormal decreased range of motion, mechanical damage, wear and tear, hypomobility, hypermobility, disc failure properties, altered cell level signals, matrix remodeling, incomplete healing, reduced motion segment function, pain, or degenerative changes; furthermore, stimulating at least one of:

neuroplasticity, neural plasticity, brain plasticity, neuroplastic changes in a body of a user, neuroplastic subluxation, proprioceptors, non-pain-producing mechanoreceptors, nociceptors, the vestibular system, afferent impulses from the periphery to the central nervous system, neurological tissue, the release of endorphins, descending inhibitory pathways, depression or inhibition of contractile tissues, depression or inhibition of pain promoting tissues comprising substance P release, the placebo effect, the Pavlovian response, or a sense of relaxation.

11. A device according to claim 8, further comprising the device undergoes motion comprising at least one of:

wobbling, rocking, rolling, pitching, yawing, shaking, vibrating, percussing, heating, sound transmitting, Brownian motion, oscillating, rubbing, kneading, scratching, massaging, rotating, linear motion, reciprocating, gliding, sliding, rectilinear motion, irregular motion, periodic motion, translatory motion, bumping, to and fro motion, or spinning.

12. A device according to claim 11, further comprising the device be coordinated with the user as a sex act support device.

13. A device according to claim 1, further comprising the at least one surface of the device comprises at least one component which is at least one of a:

ribbed, textured, smooth, undulating, knobbed, ridged, protruded, indented, retractable, telescoping, sound producing, sound emitting, microphone enabled, light emitting, laser emitting, photobiomodulation emitting, ultrasound emitting, ultraviolet light emitting, vibrating, infrared emitting, heating, percussing, electromagnetic spectrum emitting, electromagnetic field emitting, electromagnetic energy emitting, ozone emitting, ion emitting, cation emitting, molecular hydrogen emitting, diatomic molecule of hydrogen emitting, electrolysis capable, magnetic field emitting, bluetooth capable, Wi-Fi capable, electronic device linking, electronic device compatible, wireless communication capable, data collecting, data emitting, data processing, data receiving, electromagnetic energy receiving, or microwave emitting surface.

14. A device according to claim 1, further comprising the device be coordinated with a user as a sex act support device.

15. A device according to claim 1, further comprising the device comprises an enclosure.

16. A device according to claim 15, further comprising the enclosure comprises at least one of:
   a bag, a padded bag, a mesh wrap, a strap, a belt, a body support, a pillow, a sleeve, a cushion, a piece of fabric, a handle, a glove, a mitt, a covering, a laminated material, a garment, or a wrap.

17. A device according to claim 9, further comprising the integration allows the device to be permanently secured, interchangeable, or removable.

18. A method of using a concave angulated device for at least one use of: passive use, active use, isometric use, stretching, supporting, bracing, rehabilitating, positioning, massaging, kneading, scratching, exercising, or neuroplasticity stimulation of a body of a user; the device comprising:
   at least one concave angulated surface, at least one base surface, at least two side surfaces that are substantially parallel to each other, and at least two other side surfaces that are substantially parallel to each other, further comprising the at least one concave angulated surface is characterized by a polyhedral presentation comprising at least two or more surfaces intersecting at one or more substantially dihedral angles comprising a cradle for a body of a user where the terminal ends of the at least one concave angulated surface are taller, relative to the base surface, than any other edge that is further comprised within the polyhedral presentation; furthermore, the mode of use of the concave angulated device is characterized by orienting the at least one concave angulated surface substantially perpendicular to and against the long axis of a portion of a user; furthermore, the concave angulated device comprises a platform for a user to resist or absorb at least one force during use.

19. The method of claim 18, further comprising the at least one use promotes an interaction between a user and the device, the interaction comprising at least one of:
   active use or passive use by a portion of a body of a user pressing against the device creating a unique concentric, eccentric, or lengthening force via the neuromusculoskeletal tissues leveraged against the at least one concave angulated surface of the device; furthermore, the interaction moves or supports a portion of a body of a user the active use or passive use comprising at least one of;
   active chin retraction,
   active pelvic tilting,
   pelvifemoral motions,
   stretches, stretching or exercising an extremity, spine, or the torso,
   proximal core exercising, active or passive spinal disc decompression, or
   a continued physical interaction between the device and a portion of a body of a user
   comprising at least an oscillating movement which translates a force into a portion of a body of a user, the movement comprising at least a massaging or kneading motion of a portion of a body of a user.

20. The method of claim 18, further comprises promoting at least one of:
   passive spinal intervertebral disc decompression, active spinal intervertebral disc decompression, passive spinal Intervertebral disc flexion distraction, active spinal intervertebral disc flexion distraction, passive spinal intervertebral disc extension distraction, active spinal intervertebral disc extension distraction, the spinal disc pump, spinal intervertebral disc imbibition, spinal intervertebral disc repair, spinal intervertebral disc hydration, spinal intervertebral disc inflammation reduction, spinal intervertebral disc debris reduction, spinal joint anatomic effects, spinal joint physiologic effects, spinal traction, joint range of motion, extremity joint anatomic effects, extremity joint physiologic effects, joint decompression, joint hydration, joint repair, joint distraction, joint traction, muscle repair, muscle stretching, muscle elongation, muscle strengthening, muscle relaxation, muscle spasm relaxation, tendon repair, tendon stretching, tendon strengthening, ligament repair, ligament strengthening, ligament stretching, cartilage repair, cartilage hydration, disrupting scar tissue, disrupting the formation of scar tissue, elongating scar tissue, elongating neurological tissues, decreasing fluid accumulation, improving fluid drainage, improving circulation, improving lactate equilibrium, improving lymphatic flow, improving tissue drainage, improving tissue elasticity, tissue repair, tissue healing, physiologic equilibrium, a beneficial mental state, a beneficial emotional state, a state of relaxation, a healthier neuromusculoskeletal system, a beneficial energetic state, or an improved spinal disc pump action to promote an improved disc imbibition action which encourages an improved spinal motor unit function and healing for at least one of:
   after disc injury, disc overloading, abnormal immobility, abnormal decreased range of motion, mechanical damage, disc dehydration, spinal motor unit dehydration, wear and tear, hypomobility, hypermobility, disc dysfunctions, altered cell level degenerative signals, disc matrix remodeling, incomplete healing, reduced motion segment function, pain, or degenerative changes;
   furthermore, stimulating in a user at least one of:
   neuroplasticity, neural plasticity brain plasticity, neuroplastic changes in a body of a user, neuroplastic subluxation, proprioceptors, non-pain-producing mechanoreceptors, nociceptors, the vestibular system, afferent impulses from the periphery to the central nervous system, neurological tissue, the release of endorphins, descending inhibitory pathways, depression or inhibition of contractile tissues, depression or inhibition of pain promoting tissues comprising substance P release, the placebo effect the Pavlovian response, an electromagnetic field, a magnetic field, or a sense of relaxation.

21. The method of claim 18, further comprising a use of the device by a user comprises the at least one use of; passive use, active use, or isometric use by a user; furthermore the use comprises at least one of:
   performing an action comprising a novel life threatening event, performing an action analogous to a bird flapping its wings to fly while resisting gravity, neuroplastic exercising, neuroplasticity stimulating, brain plasticity stimulating, promoting a beneficial energetic state, promoting a beneficial stimulation to address traumatic brain trauma issues, promoting a beneficial stimulation to address post-traumatic stress issues, promoting a beneficial stimulation to address concussion issues, balancing, stretching, supporting, bracing, rehabilitating, positioning, massaging, kneading, scratching, exercising, psoas muscle exercising, psoas muscle stretching, psoas muscle repairing, iliopsoas muscle exercising, iliopsoas muscle stretching, iliopsoas muscle repairing, shoulder exercising, shoulder stretching, rotator cuff exercising, rotator cuff stretching, elbow exercising, elbow stretching, wrist exercising, wrist stretching, hand exercising, hand stretching, finger exercising, finger stretching, hip exercising, hip stretching, knee exercising, knee stretching, ankle exercising, ankle stretching, foot exercising, foot stretching, plantar fascia exercising, plantar fascia stretching, toe exercising, toe stretching, pelvic tilting, core exercising, pelvic tilting from core muscular activity, chin retractions, spinal exercising, spinal stretching, spinal decompressing, spinal tractioning, spinal range of motion exercising, extremity exercising, extremity stretching, extremity joint stretching, extremity joint distracting, extremity joint labral decompressing, extremity joint exercising, extremity joint tractioning, extremity joint range of motion exercising, supporting, positioning, gliding, oscillating, rubbing, sliding, rolling, rocking, wobbling, sitting, reclining, lying, walking, running, hiking, backpacking, carrying a travel pack, wearing a fanny pack, carrying a child carrier, carrying a pet carrier, carrying a mail carrier's pack, carrying a backpack, carrying a firefighter's pack, carrying a military field pack, carrying a military pack, carrying a rucksack, carrying a military weapon, wielding a military weapon, wielding a weapon, carrying a weapon, carrying furniture carving appliances, carving equipment, carving a scuba pack, scuba diving, auxiliary air tank supporting, motorcycle riding, biking, bicycling, tricycling, vehicle or craft piloting, vehicle driving, massaging, kneading body tissues, sleeping, meditating, performing yoga, performing a sex act, performing tai chi, resting, kite surfing, surfboarding, windsurfing, parasailing, parachuting, firefighting, balancing, strengthening, rowing, using an ergometer, using a harness to transfer a person, using a harness to transfer a patient, using a rowing machine, rowing a boat, rowing a scull, kayaking, pet neuromusculoskeletal care, performing neuromusculoskeletal care on an animal, performing veterinary neuromusculoskeletal animal care, enabling an animal to perform self-rubbing against the device, an animal self-rubbing device for the purpose of revealing a habit or collecting diagnostic information to aid a animal caregiver, an animal grooming device, tissue impingement decompressing, weight lifting, bench pressing, proximal core exercising, distal core exercising, proximal spinal exercising, intervertebral disc decompressing, active intervertebral disc decompressing, spinal tractioning, pain reducing movements, pain reducing positions, pain reducing neuroplasticity stimulation, or health recovering.

22. The method of claim 18, further comprising at least one use of the device by a user comprises at least one of; isometric, passive or active use by the user.

23. The method of claim 18, further comprising the at least one use comprises at least one of passive or active action by an apparatus while integrated with the device.

24. A device according to claim 1, further comprising the mode of use of the device by a user comprises inducing the perception of a novel life threatening event.

25. A device according to claim 24, further comprising the perception of a novel, unanticipated, or unexpected life threatening event is one of:
losing balance, being overwhelmed by a force, being overwhelmed by gravity, being overwhelmed by a sensory input tipping, falling, being injured, being frightened, being overwhelmed emotionally, dying, being overwhelmed by active or passive physical resistance, or pending doom; further comprises inducing a neuroplasticity stimulation of a body of a user.

26. A device according to claim 1, further comprising the at least one concave angulated surface functions, during the interaction of the device and a user, as at least one of: a fulcrum, a lever, a force disperser, or a force concentrator.

27. A device according to claim 1, further comprising the surfaces of the concave angulated device are manufactured to further comprise variable dimensions or variable sizes substantially specific to facilitate at least one use of the device.

28. A device according to claim 1, further comprising the at least one concave angulated surface is characterized by a polyhedral presentation comprising at least six or more surfaces that are intersecting; and furthermore comprise at least three or more substantially dihedral angles comprising at least three or more concave angulated surfaces comprising a cradle for a body of a user.

29. A device according to claim 1, further comprising the at least one concave angulated surface comprises a substantially one hundred and forty six degree dihedral obtuse angle at the intersection of the at least two or more surfaces comprising the at least one concave angulated surface; furthermore, the at least one concave angulated surface comprises an intersection at a substantially seventy three degree acute angle formed by the junction of each of the terminal ends of the at least one concave angulated surface with each of the tallest vertices, relative to the base surface, of the at least two side surfaces that are substantially parallel to each other.

* * * * *